(12) United States Patent
Barron et al.

(10) Patent No.: US 11,583,507 B2
(45) Date of Patent: Feb. 21, 2023

(54) DIRECT AMPK ACTIVATOR COMPOUNDS

(71) Applicant: SOCIETE DES PRODUITS NESTLE S.A., Vevey (CH)

(72) Inventors: Denis Marcel Barron, Lutry (CH); Yann Ratinaud, Morges (CH); Kei Sakamoto, Copenhagen (DK); Matthew Sanders, Epalinges (CH); Robin Willows, Echandens (CH)

(73) Assignee: Societe des Produits Nestle S.A., Vevey (CH)

( * ) Notice: Subject to any disclaimer, the term of this patent is extended or adjusted under 35 U.S.C. 154(b) by 48 days.

(21) Appl. No.: 17/044,679

(22) PCT Filed: May 15, 2019

(86) PCT No.: PCT/EP2019/062403
§ 371 (c)(1),
(2) Date: Oct. 1, 2020

(87) PCT Pub. No.: WO2019/228794
PCT Pub. Date: Dec. 5, 2019

(65) Prior Publication Data
US 2021/0038536 A1 Feb. 11, 2021

(30) Foreign Application Priority Data
May 31, 2018 (EP) ..................................... 18175282

(51) Int. Cl.
*A61K 31/085* (2006.01)
*A61K 31/05* (2006.01)

(52) U.S. Cl.
CPC ............ *A61K 31/085* (2013.01); *A61K 31/05* (2013.01)

(58) Field of Classification Search
CPC .... A61K 31/366; A61K 31/085; A61K 31/05; A61P 25/28
See application file for complete search history.

(56) References Cited

FOREIGN PATENT DOCUMENTS

| CN | 101843627 | 9/2010 |
| CN | 106928034 | 7/2017 |
| EP | 0363128 | 4/1990 |
| JP | 0717857 | 1/1995 |
| KR | 20090052752 | 5/2009 |
| KR | 20140108796 | 9/2014 |
| WO | 2009047791 | 4/2009 |

OTHER PUBLICATIONS

Liang et al. (Oncotarget, vol. 8, 37, 62780-792). (Year: 2017).*
Klongkumnuankarn et al. "Cytotoxic and Antimigratory Activities of Phenolic Compounds from Dendrobium brymerianum" Evidence-Based Complementary and Alternative Medicine, 2015, vol. 2015, pp. 1-9.
Williams et al. "Isolation of Apoptosis-Inducing Stilbenoids from Four Members of the Orchidaceae Family" Planta Medica, 2011, vol. 78, No. 02, pp. 160-165.
Liu et al. "Study on the structures and anti-hepatic fibrosis of stilbenoids from Arundina graminifolia (D. Don) Hochr." I O P Conference Series: Materials Science and Engineering, 2017, vol. 274, p. 012024.
Gui-Yun et al. "New phenanthrene and 9,10-dihydrophenanthrene derivatives from the stems of Dendrobium officinale with their cytotoxic activities" Natural Medicines—Shoyakugaku Zasshi, Japanese Society of Pharmacognosy, Tokyo, JP, 2017, vol. 72, No. 1, pp. 246-251.
Yang et al. "Antifibrotic Phenanthrenes of Dendrobium nobile Stems" Journal of Natural Products, 2007, vol. 70, No. 12, pp. 1925-1929.
Pakakrong et al. "A novel steroid and cytotoxic constituents fromDioscorea membranaceaPierre against hepatocellular carcinoma and cholangiocarcinoma cells" Journal of Ethnopharmacology, Elsevier Ireland Ltd., IE, 2016, vol. 194, pp. 91-97.
Boger et al. "Antimicrobials and antitumor properties of 9,10-dihydrophenanthrenes: structure activity studies and juncusol" Journal of Medicinal Chemistry, 1985, pp. 1543-1547.
Shriram V et al. "Cytotoxic activity of 9,10-dihydro-2,5-dimethoxyphenanthrene-1,7-diol from Eulophia nuda against human cancer cells" Journal of Ethnopharmacology, Elsevier, Ireland Ltd., IE, 2010, vol. 128, No. 1, pp. 251-253.
Apel et al. "Phenanthrene derivatives from Apendicula reflexa as new CDK1/cyclin B inhibitors" Phytochemistry Letters, 2012, vol. 5, No. 4, pp. 814-818.
Wang, Guanghui et al. "Study on cytotoxicity of four 9,10-dihydrophenanthrenes" Chemical Abstracts Service, Columbus, Ohio, US, XP002792916, Abstract.
Arunporn et al. "Isolation and characterization of a new cytotoxic dihydrophenanthrene fromDioscorea membranacearhizomes and its activity against five human cancer cell lines" Journal of Ethnopharmacology, Elsevier Ireland Ltd, IE, 2014, vol. 156, pp. 130-134.
Hu et al. "Chemical Components of Dendrobium polyanthum" Bulletin of the Korean Chemical Society, 2009, pp. 2098-2100.

* cited by examiner

*Primary Examiner* — Umamaheswari Ramachandran
(74) *Attorney, Agent, or Firm* — K&L Gates LLP

(57) ABSTRACT

The present invention relates to a compound having general formula I for use in the activation of AMPK. A composition comprising said compound for use in the activation of AMPK is also provided. Said compounds are 9,10 dihydrophenanthrenes, in particular selected from the group consisting of: (i) Lusianthridin i.e. 7-Methoxy-9,10-dihydrophenanthrene-2,5-diol, (ii) 7-Methoxy-9,10-dihydrophenanthrene-2,3,5-triol, (iii) 9,10-dihydrophenanthrene-2,5-diol, (iv) 9,10-Dihydrophenanthrene-2,4,7-triol (v) 9,10-Dihydro-7-methoxy-3,5-phenanthrenediol, and the activation of AMPK improves the condition, disorder, or disease related to cardiometabolic health, obesity, type 2 diabetes, non-alcoholic fatty liver disease, cardiovascular disease, and cancer.

18 Claims, 20 Drawing Sheets a) HTRF assay b) Western blot analysis

DIRECT AMPK ACTIVATOR COMPOUNDS

CROSS REFERENCE TO RELATED APPLICATIONS

The present application is a National Stage of International Application No. PCT/EP2019/062403, filed on May 15, 2019, which claims priority to European Patent Application No. 18175282.5, filed on May 31, 2018, the entire contents of which are being incorporated herein by reference.

INTRODUCTION

AMP-activated protein kinase (AMPK) is an evolutionarily conserved master regulator of energy homeostasis that coordinates metabolic pathways in order to balance nutrient supply with energy demand. AMPK is considered a key drug target to combat the growing epidemic of metabolic disorders such as obesity, type 2 diabetes, cardiovascular disease. AMPK activity is found in all tissues, including liver, kidney, muscle, lung, and brain (PMID: 10698692). In terms of structure, AMPK is a heterotrimeric complex consisting of a catalytic subunit (α) and two regulatory subunits ((β and γ). The AMPK complex is evolutionarily conserved and also can be found in yeast and plants. Mammalian AMPK is composed of different isoforms of subunits: α1, α2, β1, β2, γ1, γ2, and γ3 (PMID: 11746230) leading to 12 possible heterotrimeric combinations. The α2 isoform is predominately found in skeletal and cardiac muscle AMPK; both the α1 and α2 isoforms are found in hepatic AMPK; while for example in adipose and T cells the α1 isoform AMPK predominates (PMID: 16818670, PMID 15878856).

Type 2 diabetes is a complex and heterogeneous disorder. There is no ubiquitously applicable single solution to treat the disease, and a combination of pharmaceutical and lifestyle interventions are recommended. Finding natural molecules that moderately activate AMPK especially in muscle and liver with defined mechanism of action are likely to provide exercise-mimetic effects and help maintain/improve metabolic health.

There is no direct AMPK-activating drug available to treat metabolic disorders despite intensive efforts continuously made by the pharmaceutical industry. There is not thought to be any clinical trials registered to test the effects of AMPK-activating drug. Several synthetic AMPK activators have been identified/developed. However, they either have no/poor oral availability (PMID: 16753576, PMID: 24900234) or there are concerns about their adverse effects, since chronic and strong AMPK activation may cause increases in cardiac glycogen content and hypertrophy (PMID: 11827995).

There are numerous natural compounds/extracts known to bring about some metabolic health benefits that are shown to indirectly stimulate AMPK most likely through inhibition of mitochondrial respiration. However, whether those metabolic effects are mediated by AMPK is largely elusive, and moreover there are concerns regarding side/toxic effects (cellular/mitochondrial poisoning).

There is a clear unmet need for new natural compounds which directly activate AMPK.

SUMMARY OF THE INVENTION

The invention provides a compound having the general formula I,

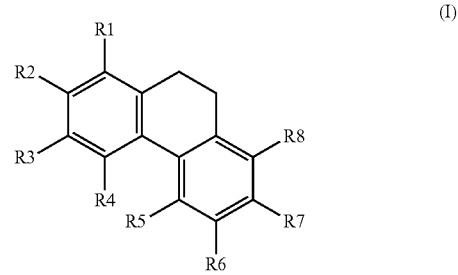

wherein R1, R2, R3, R4, R5, R6, R7, and R8 are each independently H; OH; OMe; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; a carboxylic acid; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1, R2, R3, R6, R7, and R8 are each independently H; OH; OMe; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; a carboxylic acid; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl; R4 and R5 are each independently H; OH; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; a carboxylic acid; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, R1, R2, R3, R4, R5, R6, R7, and R8 are each independently H; OH; OMe; O-glycoside; a halogen; an aldehyde; a carboxylic acid; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, or a derivative or analogue thereof, for use in the activation of AMPK.

In one embodiment, R2 is H; OH; OMe; O-glycoside; an optionally substituted and/or optionally branched C1 to C10 alkyl; an optionally substituted and/or optionally branched, C2 to C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl or a derivative or analogue thereof, for use in the activation of AMPK.

In one embodiment, R4 is H; OH; O-glycoside; an optionally substituted and/or optionally branched C1 to C10 alkyl; an optionally substituted and/or optionally branched, C2-C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl or a derivative or analogue thereof, for use in the activation of AMPK.

In one embodiment, R5 is H; OMe; O-glycoside; an optionally substituted and/or optionally branched C1 to C10 alkyl; an optionally substituted and/or optionally branched, C2-C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl or a derivative or analogue thereof, for use in the activation of AMPK.

In one embodiment, R5 is H; O-glycoside; an optionally substituted and/or optionally branched C1 to C10 alkyl; an optionally substituted and/or optionally branched, C2-C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl or a derivative or analogue thereof, for use in the activation of AMPK.

In one embodiment, R6 is H; OH; O-glycoside; an optionally substituted and/or optionally branched C1 to C10 alkyl; an optionally substituted and/or optionally branched, C2-C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl or a derivative or analogue thereof, for use in the activation of AMPK.

In one embodiment, R7 is H; OH; O-glycoside; an optionally substituted and/or optionally branched C1 to C10 alkyl; an optionally substituted and/or optionally branched, C2-C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl or a derivative or analogue thereof, for use in the activation of AMPK.

In one embodiment, R2 is H; OH; OMe; O-glycoside; an optionally substituted and/or optionally branched C1 to C10 alkyl; an optionally substituted and/or optionally branched, C2-C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl; R4 is H; OH; O-glycoside; an optionally substituted and/or optionally branched C1 to C10 alkyl; an optionally substituted and/or optionally branched, C2-C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl; and R7 is H; OH; O-glycoside; an optionally substituted and/or optionally branched C1 to C10 alkyl; an optionally substituted and/or optionally branched, C2-C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl or a derivative or analogue thereof, for use in the activation of AMPK.

In one embodiment, R2 is H; OH; OMe; O-glycoside; an optionally substituted and/or optionally branched C1 to C5 alkyl; an optionally substituted and/or optionally branched, C2-C5 alkenyl; an optionally substituted and/or optionally branched, C4 to C10 polyalkenyl; an optionally substituted and/or optionally branched C2 to C5 alkynyl, or an optionally substituted and/or optionally branched C4 to C5 polyalkynyl; R4 is H; OH; O-glycoside; an optionally substituted and/or optionally branched C1 to C5 alkyl; an optionally substituted and/or optionally branched, C2-C5 alkenyl; an optionally substituted and/or optionally branched, C4 to C10 polyalkenyl; an optionally substituted and/or optionally branched C2 to C5 alkynyl, or an optionally substituted and/or optionally branched C4 to C5 polyalkynyl; and R7 is H; OH; O-glycoside; an optionally substituted and/or optionally branched C1 to C5 alkyl; an optionally substituted and/or optionally branched, C2-C5 alkenyl; an optionally substituted and/or optionally branched, C4 to C5 polyalkenyl; an optionally substituted and/or optionally branched C2 to C5 alkynyl, or an optionally substituted and/or optionally branched C4 to C5 polyalkynyl or a derivative or analogue thereof, for use in the activation of AMPK.

In one embodiment, R2 is H; OH; OMe; O-glycoside; a C1 to C5 alkyl; a C2 to C5 alkenyl; a C4 to C5 polyalkenyl; a C2 to C5 alkynyl, or C4 to C5 polyalkynyl; R4 is H; OH; O-glycoside; a C1 to C5 alkyl; a C2-C5 alkenyl; a C4 to C5 polyalkenyl; a C2 to C5 alkynyl, or a C4 to C5 polyalkynyl; and R7 is H; OH; O-glycoside; a C1 to C5 alkyl; a C2 to C5 alkenyl; a C4 to C5 polyalkenyl; a C2 to C5 alkynyl; or a C4 to C5 polyalkynyl or a derivative or analogue thereof, for use in the activation of AMPK.

In one embodiment, the alkyl, alkenyl, and alkynyl is unbranched.

In one embodiment, the alkyl, alkenyl, and alkynyl is unsubstituted.

In some embodiments, a OCH3 group can cyclize with a neighboring OH group to form a methylene dioxy bridge.

In one embodiment, R1, R2, R3, R6, R7, and R8 are each independently H; OH; OMe; O-glycoside; a halogen; an aldehyde; a carboxylic acid; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl; R4 and R5 are each independently H; OH; O-glycoside; a halogen; an aldehyde; a carboxylic acid; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl or a derivative or analogue thereof, for use in the activation of AMPK.

In some embodiments, a OCH3 group can cyclize with a neighboring OH group to form a methylene dioxy bridge.

In one embodiment, R1, R2, R3, R4, R5, R6, R7, and R8 are each independently H; Me; OH; OMe; OCH2CH=CH2; O-glycoside; a sulfate; a halogen; CHO; CH2OH; COOH, CONH2, COCH3; CH=CH2; CH2-CH=C(CH3)2; CH(CH3)2; CH=CH—CHO; CH(CH3)-OH; CH(CH3)-OMe; CH(CH3)-OC2H5; CH(CH3)-O—CH2-CH=C(CH3)-(CH2)3-CH(CH3)-(CH2)3-CH(CH3)-(CH2)3-CH(CH3)2; 4-hydroxybenzyl; 4-hydroxy-3-methoxybenzyl; 4-hydroxybenzoyl; 4-hydroxybenzoyl glycoside or a derivative or analogue thereof, for use in the activation of AMPK.

In some embodiments, a OCH3 group can cyclize with a neighboring OH group to form a methylene dioxy bridge.

In one embodiment, R1, R2, R3, R6, R7, and R8 are each independently H; Me; OH; OMe; OCH2CH=CH2; O-glycoside; a sulfate; a halogen; CHO; CH2OH; COOH, CONH2, COCH3; CH=CH2; CH2-CH=C(CH3)2; CH(CH3)2; CH=CH—CHO; CH(CH3)-OH; CH(CH3)-OMe; CH(CH3)-OC2H5; CH(CH3)-O—CH2-CH=C(CH3)-(CH2)3-CH(CH3)-(CH2)3-CH(CH3)-(CH2)3-CH(CH3)2; 4-hydroxybenzyl; 4-hydroxy-3-methoxybenzyl; 4-hydroxybenzoyl; 4-hydroxybenzoyl glycoside; R4 and R5 are each independently H; Me; OH; OCH2CH=CH2; O-glycoside; a sulfate; a halogen; CHO; CH2OH; COOH, CONH2, COCH3; CH=CH2; CH2-CH=C(CH3)2; CH(CH3)2; CH=CH—CHO; CH(CH3)-OH; CH(CH3)-OMe; CH(CH3)-OC2H5; CH(CH3)-O—CH2-CH=C(CH3)-(CH2)3-CH(CH3)-(CH2)3-CH(CH3)-(CH2)3-CH(CH3)2; 4-hydroxybenzyl; 4-hydroxy-3-methoxybenzyl; 4-hydroxybenzoyl; 4-hydroxybenzoyl glycoside or a derivative or analogue thereof, for use in the activation of AMPK.

In some embodiments, a OCH3 group can cyclize with a neighboring OH group to form a methylene dioxy bridge.

In one embodiment, R1, R2, R3, R4, R5, R6, R7, and R8 are each independently H; Me; OH; OMe; OCH2CH=CH2; O-glycoside; a sulfate; Br; CHO; CH2OH; COOH, CONH2, COCH3; CH=CH2; CH2-CH=C(CH3)2; CH(CH3)2; CH=CH—CHO; CH(CH3)-OH; CH(CH3)-OCH3; CH(CH3)-OC2H5; CH(CH3)-O—CH2-CH=C(CH3)-(CH2)3-CH(CH3)-(CH2)3-CH(CH3)-(CH2)3-CH(CH3)2; 4-hydroxybenzyl; 4-hydroxy-3-methoxybenzyl; 4-hydroxybenzoyl; 4-hydroxybenzoyl glycoside or a derivative or analogue thereof, for use in the activation of AMPK.

In some embodiments, a OCH3 group can cyclize with a neighboring OH group to form a methylene dioxy bridge.

In one embodiment, R1, R2, R3, R6, R7, and R8 are each independently H; Me; OH; OMe; OCH2CH=CH2; O-glycoside; a sulfate; Br; CHO; CH2OH; COOH, CONH2, COCH3; CH=CH2; CH2-CH=C(CH3)2; CH(CH3)2; CH=CH—CHO; CH(CH3)-OH; CH(CH3)-OCH3; CH(CH3)-OC2H5; CH(CH3)-O—CH2-CH=C(CH3)-(CH2)3-CH(CH3)-(CH2)3-CH(CH3)-(CH2)3-CH(CH3)2; 4-hydroxybenzyl; 4-hydroxy-3-methoxybenzyl; 4-hydroxybenzoyl; 4-hydroxybenzoyl glycoside; R4 and R5 are each independently H; Me; OH; OCH2CH=CH2; O-glycoside; a sulfate; Br; CHO; CH2OH; COOH, CONH2, COCH3; CH=CH2; CH2-CH=C(CH3)2; CH(CH3)2; CH=CH—CHO; CH(CH3)-OH; CH(CH3)-OCH3; CH(CH3)-OC2H5; CH(CH3)-O—CH2-CH=C(CH3)-(CH2)3-CH(CH3)-(CH2)3-CH(CH3)-(CH2)3-CH(CH3)2; 4-hydroxybenzyl; 4-hydroxy-3-methoxybenzyl; 4-hydroxybenzoyl; 4-hydroxybenzoyl glycoside or a derivative or analogue thereof, for use in the activation of AMPK.

In some embodiments, a OCH3 group can cyclize with a neighboring OH group to form a methylene dioxy bridge.

In one embodiment, R1, R2, R3, R4, R5, R6, R7, and R8 are each independently H; Me; OH; OMe; O-glycoside; a sulfate; CH2-CH=C(CH3)2.

In some embodiments, a OCH3 group can cyclize with a neighboring OH group to form a methylene dioxy bridge.

In one embodiment, R1, R2, R3, R6, R7, and R8 are each independently H; Me; OH; OMe; O-glycoside; a sulfate; CH2-CH=C(CH3)2; R4 and R5 are each independently H; Me; OH; O-glycoside; a sulfate; CH2-CH=C(CH3)2.

In some embodiments, a OCH3 group can cyclize with a neighboring OH group to form a methylene dioxy bridge.

In one embodiment, R1 is H; CH3; OH; OCH3; O-glycoside; a sulfate; CH2-CH=C(CH3)2; 4-hydroxybenzyl; 4-hydroxy-3-methoxybenzyl; 4-hydroxybenzoyl; or 4-hydroxybenzoyl glycoside; R2 and R7 are each independently OH; OCH3; O—CH=CH2; O-glycoside; or a sulfate; R3 is H; CH3; OH; OCH3; O-glycoside; a sulfate; CH2-CH=C(CH3)2; or 4-hydroxybenzyl; R4 and R5 are each independently OH, OCH3; O-glycoside; or a sulfate; R6 is CH3; OH; OCH3; O-glycoside; CH2-CH=C(CH3)2; 4-hydroxybenzyl; or Ar; R8 is OH: OCH3; O-glycoside; a sulfate; CH2-CH=C(CH3)2; or 4-hydroxybenzyl, In one embodiment, R7 is H; CH3; OH; OCH3; O-glycoside; a sulfate; CH2-CH=C(CH3)2; 4-hydroxybenzyl; 4-hydroxy-3-methoxybenzyl; 4-hydroxybenzoyl; or 4-hydroxybenzoyl glycoside; R2 and R7 are each independently OH; OCH3; O—CH=CH2; O-glycoside; or a sulfate; R3 is H; CH3; OH; OCH3; O-glycoside; a sulfate; CH2-CH=C(CH3)2; or 4-hydroxybenzyl; R4 and R5 are each independently OH, O-glycoside; or a sulfate; R6 is CH3; OH; OCH3; O-glycoside; CH2-CH=C(CH3)2; 4-hydroxybenzyl; or Ar; R8 is OH: OCH3; O-glycoside; a sulfate; CH2-CH=C(CH3)2; or 4-hydroxybenzyl.

In one embodiment, R1, R3, R5, R6, and R8 is H; R2 is OH; OMe, or O-glycoside; R4 is OH, or O-glycoside; and R7 is OH, or O-glycoside.

In one embodiment, R1, R3, R5, R6, and R8 is H; R2 is OH or OMe; R4 is OH; and R7 is OH.

In one embodiment, R1, R3, R5, R6, and R8 is H; R2 is OMe; R4 is OH; and R7 is OH.

In one embodiment, said compound is Lusianthridin known as 7-Methoxy-9,10-dihydrophenanthrene-2,5-diol with a CAS number 87530-30-1.

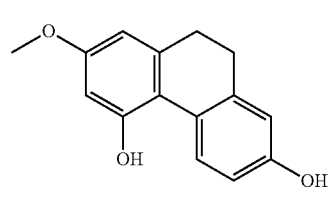

Lusianthridin

In another embodiment, said compound is compound 2 known as 7-Methoxy-9,10-dihydrophenanthrene-2,3,5-triol.

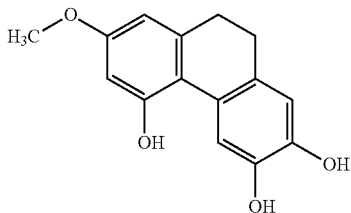
Compound 2

In another embodiment, said compound is compound 3 known as 2,5-Phenanthrenediol, 9,10-dihydro, 9,10-Dihydrophenanthrene-2,5-diol, with a CAS number 1071055-42-9.

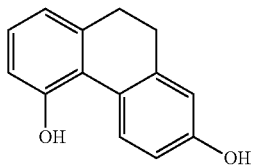
Compound 3

In another embodiment, said compound is compound 4 known as 9,10-Dihydrophenanthrene-2,4,7-triol, 9,10-Dihydro-2,4,7-phenanthrenetriol, 2,4,7-Trihydroxy-9,10-dihydrophenanthrene, 2,4,7-Phenanthrenetriol, 9,10-dihydro with a CAS number 70205-52-6.

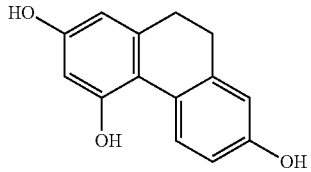
Compound 4

In another embodiment, said compound is compound 5 known as Cannithrene 1, Cannabidihydrophenanthrene, 9,10-Dihydro-7-methoxy-3,5-phenanthrenediol, 3,5-Phenanthrenediol, 9,10-dihydro-7-methoxy, 7-Methoxy-9,10-dihydrophenanthrene-3,5-diol, with a CAS number 71135-80-3.

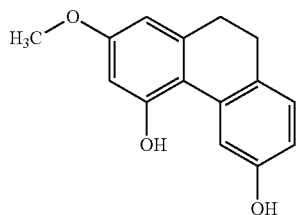
Compound 5

In one embodiment, the activation of AMPK treats or prevents a condition, disorder, or disease in a subject.

In one embodiment, the subject is a human or companion animal.

In one embodiment, the subject is a human.
In one embodiment, the subject is an older human.
In one embodiment, the subject is an elderly human.
In one embodiment, the subject is a companion animal.
In one embodiment, the condition, disorder, or disease relates to cardiometabolic health, obesity, type 2 diabetes, non-alcoholic fatty liver disease, cardiovascular disease, and/or cancer.

In one embodiment, the condition, disorder, or disease relates to type 2 diabetes and/or non-alcoholic fatty liver disease.

In one embodiment, the activation of AMPK is a direct activation mechanism.

In one embodiment, the activation of AMPK is in muscle and liver tissues.

In one embodiment, the AMPK comprises an α2 subunit, a β1 subunit, and a γ1 subunit.

In one embodiment, the AMPK comprises an α1 subunit, a β1 subunit, and a γ1 subunit.

In one embodiment, said compound is obtained from a plant or plant extract.

In one embodiment, said compound is obtained by chemical synthesis.

The present invention also provides a compound of general formula I as described herein for use in the preparation of a medicament for, treating or preventing a condition, disorder, or disease responsive to AMPK activation.

In one embodiment, the compound of general formula I is for use in the preparation of a medicament for treating or preventing type 2 diabetes.

In one embodiment, the compound of general formula I is for use in the preparation of a medicament for treating or preventing non-alcoholic fatty liver disease.

The present invention also provides a composition comprising a compound of general formula I as described herein, or a derivative or an analogue thereof, for use in the activation of AMPK.

In one embodiment, the composition is a food, beverage, or dietary supplement.

In one embodiment, the composition is a nutraceutical.

In one preferred embodiment, the compound of general formula I is Lusianthridin known as 7-Methoxy-9,10-dihydrophenanthrene-2,5-diol with a CAS number 87530-30-1.

In one preferred embodiment, the compound of general formula I is compound 2 known as 7-Methoxy-9,10-dihydrophenanthrene-2,3,5-triol.

In one preferred embodiment, the compound of general formula I is compound 3 known as 2,5-Phenanthrenediol, 9,10-dihydro, 9,10-Dihydrophenanthrene-2,5-diol, with a CAS number 1071055-42-9.

In one preferred embodiment, the compound of general formula I is compound 4 known as 9,10-Dihydrophenanthrene-2,4,7-triol, 9,10-Dihydro-2,4,7-phenanthrenetriol, 2,4,7-Trihydroxy-9,10-dihydrophenanthrene, 2,4,7-Phenanthrenetriol, 9,10-dihydro, with a CAS number 70205-52-6.

In one preferred embodiment, the compound of general formula I is compound 5 known as Cannithrene 1, Cannabidihydrophenanthrene, 9,10-Dihydro-7-methoxy-3,5-phenanthrenediol, 3,5-Phenanthrenediol, 9,10-dihydro-7-methoxy, 7-Methoxy-9,10-dihydrophenanthrene-3,5-diol, with a CAS number 71135-80-3.

In one embodiment, the composition further comprises a pharmaceutically acceptable carrier.

The present invention also provides a pharmaceutical composition comprising a therapeutically effective amount of the compound of general formula I as described herein, or a pharmaceutically acceptable salt or solvate thereof, as active ingredient, and a pharmaceutically acceptable carrier, for use in the activation of AMPK.

In one preferred embodiment, the pharmaceutical composition comprising a compound of general formula I is Lusianthridin known as 7-Methoxy-9,10-dihydrophenanthrene-2,5-diol with a, CAS number 87530-30-1).

In one preferred embodiment, the pharmaceutical composition comprising a compound of general formula I is compound 2 known as 7-Methoxy-9,10-dihydrophenanthrene-2,3,5-triol.

In one preferred embodiment, the pharmaceutical composition comprising a compound of general formula I is compound 3 known as 2,5-Phenanthrenediol, 9,10-dihydro-, 9,10-Dihydrophenanthrene-2,5-diol, with a CAS number 1071055-42-9.

In one preferred embodiment, the pharmaceutical composition comprising a compound of general formula I is compound 4 known as 9,10-Dihydrophenanthrene-2,4,7-triol, 9,10-Dihydro-2,4,7-phenanthrenetriol, 2,4,7-Trihydroxy-9,10-dihydrophenanthrene, 2,4,7-Phenanthrenetriol, 9,10-dihydro, with a CAS number 70205-52-6).

In one preferred embodiment, the pharmaceutical composition comprising a compound of general formula I is compound 5 known as Cannithrene 1, Cannabidihydrophenanthrene, 9,10-Dihydro-7-methoxy-3,5-phenanthrenediol, 3,5-Phenanthrenediol, 9,10-dihydro-7-methoxy, 7-Methoxy-9,10-dihydrophenanthrene-3,5-diol, with a CAS number 71135-80-3.

In one embodiment, the pharmaceutical composition is an oral dosage form.

The present invention also provides a method of administering a therapeutically effective amount of a compound of general formula I as described herein for treating or preventing a condition, disorder, or disease responsive to AMPK activation.

In one preferred embodiment, the compound of general formula I is Lusianthridin known as 7-Methoxy-9,10-dihydrophenanthrene-2,5-diol with a, CAS number 87530-30-1).

In one preferred embodiment, the compound of general formula I is compound 2 known as 7-Methoxy-9,10-dihydrophenanthrene-2,3,5-triol.

In one preferred embodiment, the compound of general formula I is compound 3 known as 2,5-Phenanthrenediol, 9,10-dihydro, 9,10-Dihydrophenanthrene-2,5-diol, with a CAS number 1071055-42-9.

In one preferred embodiment, the compound of general formula I is compound 4 known as 9,10-Dihydrophenanthrene-2,4,7-triol, 9,10-Dihydro-2,4,7-phenanthrenetriol, 2,4,7-Trihydroxy-9,10-dihydrophenanthrene, 2,4,7-Phenanthrenetriol, 9,10-dihydro, with a CAS number 70205-52-6).

In one preferred embodiment, the compound of general formula I is compound 5 known as Cannithrene 1, Cannabidihydrophenanthrene, 9,10-Dihydro-7-methoxy-3,5-phenanthrenediol, 3,5-Phenanthrenediol, 9,10-dihydro-7-methoxy, 7-Methoxy-9,10-dihydrophenanthrene-3,5-diol, with a CAS number 71135-80-3.

In one embodiment, the disorder responsive to AMPK activation is a metabolic disorder.

In one embodiment, the metabolic disorder is pre-diabetes or diabetes.

In one embodiment, the metabolic disorder of diabetes is accompanied by conditions which may be responsive to AMPK activation, for example, diabetic nephropathy or diabetic neuropathy.

In one embodiment, the metabolic disorder is dyslipidemia.

The present invention also provides a method for activating AMPK in a subject in need thereof, said method comprising administering to the subject in need a composition comprising an effective amount of a compound of general formula I as described herein.

In one preferred embodiment, the compound of general formula I is Lusianthridin known as 7-Methoxy-9,10-dihydrophenanthrene-2,5-diol with a, CAS number 87530-30-1.

In one preferred embodiment, the compound of general formula I is compound 2 known as 7-Methoxy-9,10-dihydrophenanthrene-2,3,5-triol.

In one preferred embodiment, the compound of general formula I is compound 3 known as 2,5-Phenanthrenediol, 9,10-dihydro, 9,10-Dihydrophenanthrene-2,5-diol, with a CAS number 1071055-42-9.

In one preferred embodiment, the compound of general formula I is compound 4 known as 9,10-Dihydrophenanthrene-2,4,7-triol, 9,10-Dihydro-2,4,7-phenanthrenetriol, 2,4,7-Trihydroxy-9,10-dihydrophenanthrene, 2,4,7-Phenanthrenetriol, 9,10-dihydro, with a CAS number 70205-52-6.

In one preferred embodiment, the compound of general formula I is compound 5 known as Cannithrene 1, Cannabidihydrophenanthrene, 9,10-Dihydro-7-methoxy-3,5-phenanthrenediol, 3,5-Phenanthrenediol, 9,10-dihydro-7-methoxy, 7-Methoxy-9,10-dihydrophenanthrene-3,5-diol, with a CAS number 71135-80-3.

The present invention also provides an in vitro method of activating AMPK, comprising contacting a compound of general formula I as described herein, or a derivative or an analogue thereof, with AMPK.

In one embodiment, the in vitro method is cell free.

In one embodiment, the in vitro method is cell based.

In one preferred embodiment, the compound of general formula I is Lusianthridin known as 7-Methoxy-9,10-dihydrophenanthrene-2,5-diol with a, CAS number 87530-30-1.

In one preferred embodiment, the compound of general formula I is compound 2 known as 7-Methoxy-9,10-dihydrophenanthrene-2,3,5-triol.

In one preferred embodiment, the compound of general formula I is compound 3 known as 2,5-Phenanthrenediol, 9,10-dihydro, 9,10-Dihydrophenanthrene-2,5-diol, with a CAS number 1071055-42-9.

In one preferred embodiment, the compound of general formula I is compound 4 known as 9,10-Dihydrophenanthrene-2,4,7-triol, 9,10-Dihydro-2,4,7-phenanthrenetriol, 2,4,7-Trihydroxy-9,10-dihydrophenanthrene, 2,4,7-Phenanthrenetriol, 9,10-dihydro, with a CAS number 70205-52-6.

In one preferred embodiment, the compound of general formula I is compound 5 known as Cannithrene 1, Cannabidihydrophenanthrene, 9,10-Dihydro-7-methoxy-3,5-phenanthrenediol, 3,5-Phenanthrenediol, 9,10-dihydro-7-methoxy, 7-Methoxy-9,10-dihydrophenanthrene-3,5-diol, with a CAS number 71135-80-3.

DETAILED DESCRIPTION

Compound Having the General Formula I

The present invention relates to a compound having the general formula I as described herein with the structure as shown below:

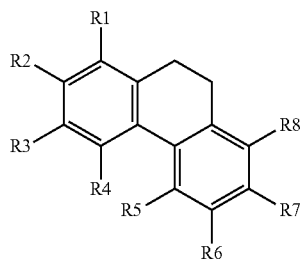

(I)

wherein R1, R2, R3, R4, R5, R6, R7, and R8 are each independently H; OH; OMe; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; a carboxylic acid; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl or a derivative or analogue thereof, for use in the activation of AMPK.

In some embodiments, a OCH3 group can cyclize with a neighboring OH group to form a methylene dioxy bridge.

In one embodiment, the invention provides a compound of general formula I wherein R1, R2, R3, R6, R7, and R8 are each independently H; OH; OMe; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; a carboxylic acid; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl; R4 and R5 are each independently H; OH; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; a carboxylic acid; an ester; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, or a derivative or analogue thereof, for use in the activation of AMPK.

In some embodiments, a OCH3 group can cyclize with a neighboring OH group to form a methylene dioxy bridge.

In one embodiment, the invention provides a compound of general formula I wherein R1, R2, R3, R4, R5, R6, R7, and R8 are each independently H; OH; OMe; O-glycoside; a halogen; an aldehyde; a carboxylic acid; a primary, secondary, or tertiary amine; a primary or secondary amide; a cyano; a nitro; a sulfonate; a sulfate; an optionally substituted and/or optionally branched C1 to C20 alkyl; an optionally substituted and/or optionally branched, C2 to C20 alkenyl; an optionally substituted and/or optionally branched, C4 to C20 polyalkenyl; an optionally substituted and/or optionally branched C2 to C20 alkynyl, or an optionally substituted and/or optionally branched C4 to C20 polyalkynyl, or a derivative or analogue thereof, for use in the activation of AMPK.

In one embodiment, the invention provides a compound of general formula I wherein R2 is H; OH; OMe; O-glycoside; an optionally substituted and/or optionally branched C1 to C10 alkyl; an optionally substituted and/or optionally branched, C2 to C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl or a derivative or analogue thereof, for use in the activation of AMPK.

In one embodiment, the invention provides a compound of general formula I wherein R4 is H; OH; O-glycoside; an optionally substituted and/or optionally branched C1 to C10 alkyl; an optionally substituted and/or optionally branched, C2-C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl or a derivative or analogue thereof, for use in the activation of AMPK.

In one embodiment, the invention provides a compound of general formula I wherein R5 is H; OMe; O-glycoside; an optionally substituted and/or optionally branched C1 to C10 alkyl; an optionally substituted and/or optionally branched, C2-C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl or a derivative or analogue thereof, for use in the activation of AMPK.

In one embodiment, the invention provides a compound of general formula I wherein R5 is H; O-glycoside; an optionally substituted and/or optionally branched C1 to C10 alkyl; an optionally substituted and/or optionally branched, C2-C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl or a derivative or analogue thereof, for use in the activation of AMPK.

In one embodiment, the invention provides a compound of general formula I wherein R6 is H; OH; O-glycoside; an optionally substituted and/or optionally branched C1 to C10 alkyl; an optionally substituted and/or optionally branched, C2-C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl or a derivative or analogue thereof, for use in the activation of AMPK.

In one embodiment, the invention provides a compound of general formula I wherein R7 is H; OH; O-glycoside; an optionally substituted and/or optionally branched C1 to C10 alkyl; an optionally substituted and/or optionally branched, C2-C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl or a derivative or analogue thereof, for use in the activation of AMPK.

In one embodiment, the invention provides a compound of general formula I wherein R2 is H; OH; OMe; O-glycoside; an optionally substituted and/or optionally branched C1 to C10 alkyl; an optionally substituted and/or optionally branched, C2-C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl; R4 is H; OH; O-glycoside; an optionally substituted and/or optionally branched C1 to C10 alkyl; an optionally substituted and/or optionally branched, C2-C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl; and R7 is H; OH; O-glycoside; an optionally substituted and/or optionally branched C1 to C10 alkyl; an optionally substituted and/or optionally branched, C2-C10 alkenyl; an optionally substituted and/or optionally branched, C4 to C10 polyalkenyl; an optionally substituted and/or optionally branched C2 to C10 alkynyl, or an optionally substituted and/or optionally branched C4 to C10 polyalkynyl or a derivative or analogue thereof, for use in the activation of AMPK.

In one embodiment, the invention provides a compound of general formula I wherein R2 is H; OH; OMe; O-glycoside; an optionally substituted and/or optionally branched C1 to C5 alkyl; an optionally substituted and/or optionally branched, C2-C5 alkenyl; an optionally substituted and/or optionally branched, C4 to C10 polyalkenyl; an optionally substituted and/or optionally branched C2 to C5 alkynyl, or an optionally substituted and/or optionally branched C4 to C5 polyalkynyl; R4 is H; OH; O-glycoside; an optionally substituted and/or optionally branched C1 to C5 alkyl; an optionally substituted and/or optionally branched, C2-C5 alkenyl; an optionally substituted and/or optionally branched, C4 to C10 polyalkenyl; an optionally substituted and/or optionally branched C2 to C5 alkynyl, or an optionally substituted and/or optionally branched C4 to C5 polyalkynyl; and R7 is H; OH; O-glycoside; an optionally substituted and/or optionally branched C1 to C5 alkyl; an optionally substituted and/or optionally branched, C2-C5 alkenyl; an optionally substituted and/or optionally branched, C4 to C5 polyalkenyl; an optionally substituted and/or optionally branched C2 to C5 alkynyl, or an optionally substituted and/or optionally branched C4 to C5 polyalkynyl or a derivative or analogue thereof, for use in the activation of AMPK.

In one embodiment, the invention provides a compound of general formula I wherein R2 is H; OH; OMe; O-glycoside; a C1 to C5 alkyl; a C2 to C5 alkenyl; a C4 to C5 polyalkenyl; a C2 to C5 alkynyl, or C4 to C5 polyalkynyl; R4 is H; OH; O-glycoside; a C1 to C5 alkyl; a C2-C5 alkenyl; a C4 to C5 polyalkenyl; a C2 to C5 alkynyl, or a C4 to C5 polyalkynyl; and R7 is H; OH; O-glycoside; a C1 to C5 alkyl; a C2 to C5 alkenyl; a C4 to C5 polyalkenyl; a C2 to C5 alkynyl; or a C4 to C5 polyalkynyl or a derivative or analogue thereof, for use in the activation of AMPK.

In one embodiment, the invention provides a compound of general formula I wherein the alkyl, alkenyl, and alkynyl is unbranched.

In one embodiment, the invention provides a compound of general formula I wherein the alkyl, alkenyl, and alkynyl is unsubstituted.

In some embodiments, a OCH3 group can cyclize with a neighboring OH group to form a methylene dioxy bridge.

In one embodiment, the invention provides a compound of general formula I wherein R1, R2, R3, R4, R5, R6, R7, and R8 are each independently H; Me; OH; OMe; OCH2CH=CH2; O-glycoside; a sulfate; a halogen; CHO; CH2OH; COOH, CONH2, COCH3; CH=CH2; CH2-CH=C(CH3)2; CH(CH3)2; CH=CH—CHO; CH(CH3)-OH; CH(CH3)-OMe; CH(CH3)-OC2H5; CH(CH3)-O—CH2-CH=C(CH3)-(CH2)3-CH(CH3)-(CH2)3-CH(CH3)-(CH2)3-CH(CH3)2; 4-hydroxybenzyl; 4-hydroxy-3-methoxybenzyl; 4-hydroxybenzoyl; 4-hydroxybenzoyl glycoside, or a derivative or analogue thereof, for use in the activation of AMPK.

In some embodiments, a OCH3 group can cyclize with a neighboring OH group to form a methylene dioxy bridge.

In one embodiment, the invention provides a compound of general formula I wherein R1, R2, R3, R4, R5, R6, R7, and R8 are each independently H; Me; OH; OMe; OCH2CH=CH2; O-glycoside; a sulfate; Br; CHO; CH2OH; COOH, CONH2, COCH3; CH=CH2; CH2-CH=C(CH3)2; CH(CH3)2; CH=CH—CHO; CH(CH3)-OH; CH(CH3)-OCH3; CH(CH3)-OC2H5; CH(CH3)-O—CH2-CH=C(CH3)-(CH2)3-CH(CH3)-(CH2)3-CH(CH3)-(CH2)3-CH(CH3)2; 4-hydroxybenzyl; 4-hydroxy-3-methoxybenzyl; 4-hydroxybenzoyl; 4-hydroxybenzoyl glycoside or a derivative or analogue thereof, for use in the activation of AMPK.

In some embodiments, a OCH3 group can cyclize with a neighboring OH group to form a methylene dioxy bridge.

In one embodiment, the invention provides a compound of general formula I wherein R1, R2, R3, R4, R5, R6, R7, and R8 are each independently H; Me; OH; OMe; O-glycoside; a sulfate; CH2-CH=C(CH3)2, or a derivative or analogue thereof, for use in the activation of AMPK.

In some embodiments, a OCH3 group can cyclize with a neighboring OH group to form a methylene dioxy bridge.

In one embodiment, the invention provides a compound of general formula I wherein R1 is H; CH3; OH; OCH3; O-glycoside; a sulfate; CH2-CH=C(CH3)2; 4-hydroxybenzyl; 4-hydroxy-3-methoxybenzyl; 4-hydroxybenzoyl; or 4-hydroxybenzoyl glycoside; R2 and R7 are each independently OH; OCH3; O—CH=CH2; O-glycoside; or a sulfate; R3 is H; CH3; OH; OCH3; O-glycoside; a sulfate; CH2-CH=C(CH3)2; or 4-hydroxybenzyl; R4 and R5 are each independently OH, OCH3; O-glycoside; or a sulfate; R6 is CH3; OH; OCH3; O-glycoside; CH2-CH=C(CH3)2; 4-hydroxybenzyl; or Ar; R8 is OH: OCH3; O-glycoside; a sulfate; CH2-CH=C(CH3)2; or 4-hydroxybenzyl or a derivative or analogue thereof, for use in the activation of AMPK.

In one embodiment, the invention provides a compound of general formula I wherein R1 is H; CH3; OH; OCH3; O-glycoside; a sulfate; CH2-CH=C(CH3)2; 4-hydroxybenzyl; 4-hydroxy-3-methoxybenzyl; 4-hydroxybenzoyl; or 4-hydroxybenzoyl glycoside; R2 and R7 are each independently OH; OCH3; O—CH=CH2; O-glycoside; or a sulfate; R3 is H; CH3; OH; OCH3; O-glycoside; a sulfate; CH2-CH=C(CH3)2; or 4-hydroxybenzyl; R4 and R5 are each independently OH, OCH3; O-glycoside; or a sulfate; R6 is CH3; OH; OCH3; O-glycoside; CH2-CH=C(CH3)2; 4-hydroxybenzyl; or Ar; R8 is OH: OCH3; O-glycoside; a sulfate; CH2-CH=C(CH3)2; or 4-hydroxybenzyl, or a derivative or analogue thereof, for use in the activation of AMPK.

In one embodiment, the invention provides a compound of general formula I wherein R1, R3, R5, R6, and R8 is H; R2 is OH; OMe, or O-glycoside; R4 is OH, or O-glycoside; and R7 is OH, or O-glycoside for use in the activation of AMPK.

In one embodiment, the invention provides a compound of general formula I wherein R1, R3, R5, R6, and R8 is H; R2 is OH or OMe; R4 is OH; and R7 is OH for use in the activation of AMPK.

In one embodiment, the invention provides a compound of general formula I wherein R1, R3, R5, R6, and R8 is H; R2 is OMe; R4 is OH; and R7 is OH for use in the activation of AMPK.

In one embodiment, said compound is Lusianthridin known as 7-Methoxy-9,10-dihydrophenanthrene-2,5-diol, with a CAS number 87530-30-1:

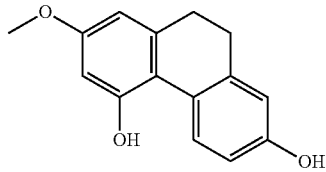

Lusianthridin

In another embodiment, said compound is compound 2 known as 7-Methoxy-9,10-dihydrophenanthrene-2,3,5-triol:

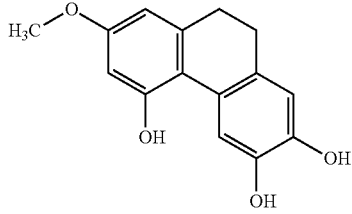

Compound 2

In another embodiment, said compound is compound 3 known as 2,5-Phenanthrenediol, 9,10-dihydro, 9,10-Dihydrophenanthrene-2,5-diol, with a CAS number 1071055-42-9:

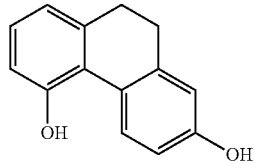

Compound 3

In another embodiment, said compound is compound 4 known as 9,10-Dihydrophenanthrene-2,4,7-triol, 9,10-Dihydro-2,4,7-phenanthrenetriol, 2,4,7-Trihydroxy-9,10-dihydrophenanthrene, 2,4,7-Phenanthrenetriol, 9,10-dihydro, with a CAS number 70205-52-6:

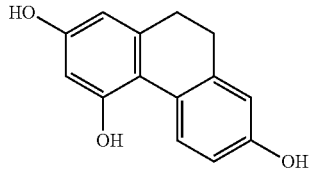

Compound 4

In another embodiment, said compound is compound 5 known as Cannithrene 1, Cannabidihydrophenanthrene, 9,10-Dihydro-7-methoxy-3,5-phenanthrenediol, 3,5-Phenanthrenediol, 9,10-dihydro-7-methoxy, 7-Methoxy-9,10-dihydrophenanthrene-3,5-diol, with a CAS number 71135-80-3:

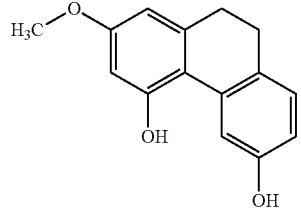

Compound 5

Definitions
General Chemistry Terminology

The term "alkyl" refers to a branched or unbranched saturated hydrocarbon chain having from 1 to 20 carbon atoms, or from 1 to 15 carbon atoms, or from 1 to 10 carbon atoms, or from 1 to 8 carbon atoms, or from 1 to 6 carbon atoms, or from 1 to 4 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl chain as defined above, having 1, 2, 3, 4 or 5 substituents, (in some embodiments, 1, 2 or 3 substituents) selected from the group consisting of alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)2-alkyl, —S(O)2-cycloalkyl, —S(O)2-heterocyclyl, —S(O)2-aryl and —S(O)2-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, and —S(O)n R<a>, in which R<a> is alkyl, aryl or heteroaryl and n is 0, 1 or 2; or 2) an alkyl chain as defined above that is interrupted by 1-10 atoms (e.g. 1, 2, 3, 4 or 5 atoms) independently chosen from oxygen, sulfur and NR<a>, where R<a> is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, and —S(O)n R<a>, in which R<a> is alkyl, aryl or heteroaryl and n is 0, 1 or 2; or 3) an alkyl chain as defined above that has both 1, 2, 3, 4 or 5 substituents as defined above and is also interrupted by 1-10 atoms (e.g. 1, 2, 3, 4 or 5 atoms) as defined above.

The term "alkenyl" refers to a type of alkyl chain in which two atoms of the alkyl group form a double bond that is not part of an aromatic group. That is, an alkenyl chain contains the pattern R—C(R)=C(R)—R, wherein R refers to the remaining portions of the alkenyl group, which may be the same or different. Non-limiting examples of an alkenyl chain include —CH=CH2, —C(CH3)=CH2, —CH=CHCH3, —C(CH3)=CHCH3, —CH2-CH=C(CH3)2, and —C(CH3)2-CH=CH2. The alkenyl moiety may be branched, straight chain, or cyclic (in which case, it would also be known as a "cycloalkenyl" group). Alkenyl groups can be optionally substituted.

The term "alkynyl" refers to a type of alkyl chain in which two atoms of the alkyl group form a triple bond. That is, an alkynyl group contains the pattern R—C≡C—R, wherein R refers to the remaining portions of the alkynyl group, which may be the same or different. Non-limiting examples of an alkynyl group include —C≡CH, —C≡CCH3 and —C≡CCH2CH3. The "R" portion of the alkynyl moiety may be branched, straight chain, or cyclic. Alkynyl groups can be optionally substituted.

The term "polyunsaturated" refers to

1) A chain known as polyalkenyl in which more than one pair of atoms of the alkyl group form a double bond that is not part of an aromatic group. That is, a polyalkenyl chain contains several R—C(R)=C(R)—R patterns, wherein R refers to the remaining portions of the alkenyl group, which may be the same or different. Non-limiting examples of a polyalkenyl chain include —CH=CH—CH=CH—, —CH2-CH=CCH3-CH2-CH2-CH=C(CH3)2, and —CH2-CH=CCH3-CH2-CH2-CH=CCH3-CH2-CH2-CH=C(CH3)2. The polyalkenyl moiety may be branched, or straight chain. The polyalkenyl moiety containing two double bond may be cyclic (in which case, it would also be known as a "cyclodialkenyl" group). Non limiting example of cyclodialkenyl groups include cyclopentadiene and cyclohexadiene groups. Polyalkenyl groups can be optionally substituted.

2) A chain known as polyalkynyl in which more than one pair of atoms of the alkyl group form a triple bond. That is, a polyalkynyl group contains several patterns R—C≡C—R, wherein R refers to the remaining portions of the alkynyl group, which may be the same or different. Non-limiting example of a polyalkynyl group include —CH2-CH2-C≡C—C≡CH. The "R" portion of the polyalkynyl moiety may be branched, straight chain, or cyclic. Alkynyl groups can be optionally substituted.

3) A type of alkyl chain in which at least one pair of atoms of the alkyl group form a double bond and one pair of atoms of the alkyl group form a triple bond. That is, a polyunsaturated chain contains both R—C(R)=C(R)—R and R—C≡C—R patterns, wherein R refers to the remaining portions of the polyunsaturated chain, which may be the same or different. Non-limiting examples this type of polyunsaturated chain include —CH2-CH=CH=CH. The "R" portion of the polyunsaturated moiety may be branched, straight chain, or cyclic. Polyunsaturated chains can be optionally substituted.

4) A polyunsaturated chain as defined above in paragraphs 1-3, that is interrupted by 1-10 atoms (e.g. 1, 2, 3, 4 or 5 atoms) independently chosen from oxygen, sulfur and NR<a>, where R<a> is chosen from hydrogen, alkyl, cycloalkyl, alkenyl, cycloalkenyl, alkynyl, aryl, heteroaryl and heterocyclyl.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can form part of a ring system. As used herein, the term "ring system" refers to two or more rings, wherein two or more of the rings are fused. The term "fused" refers to structures in which two or more rings share one or more bonds.

The term "halogen atom" may refer to a fluorine atom, a chlorine atom, a bromine atom or an iodine atom.

The term "glycoside" refers to a compound in which at least one sugar is bound to another functional group via a glycosidic bond. Typically the glycosidic chain can comprise 1 to 4 sugar units.

The term "glycosidic bond" refers to a bond formed between the hemiacetal or hemiketal group of a sugar and the chemical group of a compound. The chemical group can be —OH (O-glycoside), or —CR1R2R3 (C-glycoside).

The terms "acylated O-glycoside" and "acylated C-glycoside" refer to a compound in which at least one hydroxyl of the glycosidic chain is esterified by an organic acid. Typical examples or organic acid may comprise acetic, substituted benzoic, cinnamic (caffeic, ferulic, p-coumaric), and/or phenylpropanoic (dihydrocaffeic) acids.

The terms "sulfated O-glycoside" and "sulfated C-glycoside" refer to a compound in which at least one hydroxyl of the glycosidic chain is esterified by sulfuric acid.

The term "methylene dioxy" may refer to functional group with the structural formula R—O—CH2-O—R', connected to the rest of a molecule by two chemical bonds.

The term "analogue" as used herein is understood to refer to a compound having a structure similar to that of another one, but differing from it in respect of a certain component. A "derivative" is a compound that arises or is actually synthesized from a parent compound by replacement of one or more atoms with another atom or group of atoms.

The components of the chemical structures described herein can be further defined as follows: the term "Unsaturated" means it contains at least one, maximum eight double bond between carbon atoms. "Dehydration" means a loss of water between two neighbouring carbons, one bearing a hydroxyl and the other bearing at least one hydrogen, leading to the formation of a double bond. "Reduction" means addition of hydrogen to a double bond, leading to the formation of a single bond, typically reduction of a carbonyl to an alcohol, or an unsaturated chain to a saturated one. Carbon oxidation may be, for example, stepwise from a methyl to an alcohol, to an aldehyde, and finally to a carboxylic acid.

As used herein, the term "aldehyde" denotes an organic compound having the general structure —C—[C(=O)]n—H or H—[C(=O)]n-H (n is 1 or more and wherein the carbon atom bonded to the-[C(=O)]-n group is not double bonded to oxygen, sulfur, selenium, or tellurium, or triple bonded to nitrogen.

As used herein, the term "amine" denotes an organic compound having a nitrogen atom single or double bonded to a carbon atom and wherein the carbon atom bonded to the nitrogen atom is devoid of a double bond to oxygen, sulfur, selenium, or tellurium or triple bonded to nitrogen. In addition, those compounds wherein the same nitrogen atom is bonded to a —C(=X)— group (X is O, S, Se, or Te) and to a carbon atom which is not double bonded to oxygen, sulfur, selenium, or tellurium, are not considered as being amines, e.g., —C—NH—C(X=)—

As used herein, the term "cyano" denotes a triple bond between an adjacent carbon and nitrogen atom.

As used herein, the term "carboxylic acid" denotes the presence of a —C(=O)OH group.

Compound or Composition Thereof

It is understood that according to certain embodiments, the compound of the invention or composition thereof may be a nutraceutical composition, pharmaceutical composition, functional food, functional nutrition product, medical food, medical nutrition product, or a dietary supplement.

The terms "nutraceutical" combines the words "nutrition" and "pharmaceutical". It is a food or food product that provides health and medical benefits, including the prevention and treatment of a condition, disorder, or disease. A nutraceutical is a product isolated or purified from foods that is generally sold in medicinal forms not usually associated with food. A nutraceutical is demonstrated to have a physiological benefit or provide protection against a condition, disorder, or disease. Such products may range from isolated nutrients, dietary supplements and specific diets to genetically engineered foods, herbal products, and processed foods such as cereals, soups, and beverages.

The term "nutraceutical" as used herein denotes usefulness in both nutritional and pharmaceutical fields of application. Thus, novel nutraceutical compositions can be used as supplements to food and beverages and as pharmaceutical formulations for enteral or parenteral application which may be solid formulations, such as capsules or tablets, or liquid formulations, such as solutions or suspensions.

The nutraceutical compositions according to the present invention may further contain protective hydrocolloids (such as gums, proteins, modified starches), binders, film-forming agents, encapsulating agents/materials, wall/shell materials, matrix compounds, coatings, emulsifiers, surface active agents, solubilising agents (oils, fats, waxes, lecithins etc.), adsorbents, carriers, fillers, co-compounds, dispersing agents, wetting agents, processing aids (solvents), flowing agents, taste-masking agents, weighting agents, jellifying agents, gel-forming agents, antioxidants and antimicrobials.

Moreover, a multi-vitamin and mineral supplement may be added to nutraceutical compositions of the invention to obtain an adequate amount of an essential nutrient, which is missing in some diets. The multi-vitamin and mineral supplement may also be useful for disease prevention and protection against nutritional losses and deficiencies due to lifestyle patterns.

The nutraceutical compositions of the invention may be in any galenic form that is suitable for administering to the body, especially in any form that is conventional for oral administration, e.g. in solid forms such as food or feed, food or feed premix, fortified food or feed, tablets, pills, granules, dragees, capsules and effervescent formulations such as powders and tablets, or in liquid forms, such as solutions, emulsions or suspensions as e.g. beverages, pastes and oily suspensions. The pastes may be incorporated in hard or soft shell capsules, whereby the capsules feature e.g. a matrix of (fish, swine, poultry, cow) gelatine, plant proteins or lignin sulfonate. Examples for other application forms are those for transdermal, parenteral or injectable administration. The dietary and pharmaceutical compositions may be in the form of controlled (delayed) release formulations.

Beverages encompass non-alcoholic and alcoholic drinks as well as liquid preparations to be added to drinking water and liquid food. Non-alcoholic drinks are e.g. soft drinks, sports drinks, fruit juices, teas and milk-based drinks Liquid foods are e.g. soups and dairy products. The nutraceutical composition comprising the compound of the invention may be added to a soft drink, an energy bar, or a candy.

If the nutraceutical composition is a pharmaceutical formulation and the composition further contains pharmaceutically acceptable excipients, diluents or adjuvants then standard techniques may be used for their formulation, as e.g. disclosed in Remington's Pharmaceutical Sciences, 20th edition Williams & Wilkins, PA, USA. For oral administration, tablets and capsules are preferably used which contain a suitable binding agent, e.g. gelatine or polyvinyl pyrrolidone, a suitable filler, e.g. lactose or starch, a suitable lubricant, e.g. magnesium stearate, and optionally further additives.

"Functional food", "functional nutrition product", "medical food" and "medical nutrition product" relate to any healthy food claimed to have a health-promoting or disease-preventing property beyond the basic function of supplying nutrients. The general category of functional foods includes processed food or foods fortified with health-promoting additives, like "vitamin-enriched" products.

The terms "food," "food product" and "food composition" or "diet product" mean a product or composition that is intended for ingestion by an individual such as a human and provides at least one nutrient to the individual. The compositions of the present disclosure, including the many embodiments described herein, can comprise, consist of, or consist essentially of the elements disclosed herein, as well as any additional or optional ingredients, components, or elements described herein or otherwise useful in a diet.

A dietary supplement, also known as food supplement or nutritional supplement, is a preparation intended to supplement the diet and provide nutrients, such as vitamins, minerals, fibre, fatty acids, or amino acids that may be missing or may not be consumed in sufficient quantities in a person's diet. Some countries define dietary supplements as foods, while in others they are defined as drugs or natural health products. Supplements containing vitamins or dietary minerals are included as a category of food in the Codex Alimentarius, a collection of internationally recognized standards, codes of practice, guidelines and other recommendations relating to foods, food production and food safety. These texts are drawn up by the Codex Alimentarius Commission, an organization that is sponsored by the Food and Agriculture Organization of the United Nations (FAO) and the World Health Organization (WHO).

Compositions intended for an animal, include food compositions to supply the necessary dietary requirements for an animal, animal treats (e.g., biscuits), and/or dietary supplements. The compositions may be a dry composition (e.g., kibble), semi-moist composition, wet composition, or any mixture thereof. In one embodiment, the composition is a dietary supplement such as a gravy, drinking water, beverage, yogurt, powder, granule, paste, suspension, chew, morsel, treat, snack, pellet, pill, capsule, tablet, or any other suitable delivery form. The dietary supplement can comprise a high concentration of the UFA and NORC, and B vitamins and antioxidants. This permits the supplement to be administered to the animal in small amounts, or in the alternative, can be diluted before administration to an animal. The dietary supplement may require admixing, or can be admixed with water or other diluent prior to administration to the animal.

"Pet food" or "pet treat compositions" comprise from about 15% to about 50% crude protein. The crude protein material may comprise vegetable proteins such as soybean meal, soy protein concentrate, corn gluten meal, wheat gluten, cottonseed, and peanut meal, or animal proteins such as casein, albumin, and meat protein. Examples of meat protein useful herein include pork, lamb, equine, poultry, fish, and mixtures thereof. The compositions may further comprise from about 5% to about 40% fat. The compositions may further comprise a source of carbohydrate. The compositions may comprise from about 15% to about 60% carbohydrate. Examples of such carbohydrates include grains or cereals such as rice, corn, milo, sorghum, alfalfa, barley, soybeans, canola, oats, wheat, and mixtures thereof. The compositions may also optionally comprise other materials such as dried whey and other dairy by-products. In some embodiments, the ash content of the composition ranges from less than 1% to about 15%, and in one aspect, from about 5% to about 10%.

The moisture content can vary depending on the nature of the composition. In a one embodiment, the composition can be a complete and nutritionally balanced pet food. In this embodiment, the pet food may be a "wet food", "dry food", or food of intermediate moisture content. "Wet food" describes pet food that is typically sold in cans or foil bags, and has a moisture content typically in the range of about 70% to about 90%. "Dry food" describes pet food which is of a similar composition to wet food, but contains a limited moisture content, typically in the range of about 5% to about 15% or 20%, and therefore is presented, for example, as small biscuit-like kibbles. In one embodiment, the compositions have moisture content from about 5% to about 20%. Dry food products include a variety of foods of various moisture contents, such that they are relatively shelf-stable and resistant to microbial or fungal deterioration or contamination. Also included are dry food compositions which are extruded food products, such as pet foods, or snack foods for companion animals.

Methods of Administration of Compound or Composition Thereof

The compound of the invention or composition thereof is preferably administered by oral administration. In some embodiments, the compound of the invention or composition thereof may be administered by intravenous administration, topical administration, parenteral administration, intraperitoneal administration, intramuscular administration, intrathecal administration, intralesional administration, intracranial administration, intranasal administration, intraocular administration, intracardiac administration, intravitreal administration, intraosseous administration, intracerebral administration, intraarterial administration, intraarticular administration, intradermal administration, transdermal administration, transmucosal administration, sublingual administration, enteral administration, sublabial administration, insufflation administration, suppository administration, inhaled administration, or subcutaneous administration.

The composition of the invention can have an acute effect that can be seen in less than one month. Additionally or alternatively, the composition can have a longterm effect, and thus various embodiments comprise administration of the composition to the individual (e.g., orally) for a time period of at least one month; preferably at least two months, more preferably at least three, four, five or six months; most preferably for at least one year. During the time period, the composition can be administered to the individual at least one day per week; preferably at least two days per week, more preferably at least three, four, five or six days per week; most preferably seven days per week. The composition can be administered in a single dose per day or in multiple separate doses per day. In one embodiment, a single dose is not less than about 100 mg. In one embodiment, a single dose is not more than about 1000 mg. In one embodiment, a single dose is between about 100 mg and about 1000 mg.

AMPK Activation Terminology

As used herein, an "AMPK activator" refers to a compound that either increases the phosphorylation of downstream substrates of (phosphorylated or not) AMPK, and/or that increases the phosphorylation of AMPK.

As used herein, a "direct AMPK activator" refers to a compound that activates AMPK via direct interaction with at least one of its subunits.

As used herein, a condition, disorder, or disease "responsive to AMPK activation" refers to one in which the symptoms would be alleviated, or the course of which would be beneficially modified, through activation of AMPK, including without limitation, a metabolic disorder, diabetes, dyslipidemia, hypertension, being overweight, and obesity. For example, the metabolic disorder of diabetes is accompanied by conditions such as diabetic nephropathy or diabetic neuropathy which may be responsive to AMPK activation.

Medical Terminology

As used herein, the term "diabetes" includes insulin-dependent diabetes mellitus (i.e. IDDM, also known as type 1 diabetes) non-insulin-dependent diabetes mellitus (i.e. NIDDM, also known as type 2 diabetes), and prediabetes. Type 1 diabetes is the result of an absolute deficiency of insulin, the hormone which regulates glucose utilization. Type 2 diabetes often occurs in the face of normal, or even elevated levels of insulin and appears to be the result of the inability of tissues to respond appropriately to insulin. This is termed "insulin resistance". Most type 2 diabetic patients are also overweight or obese. One of the criteria for diagnosing diabetes is the fasting plasma glucose level. A diabetic subject has a fasting plasma glucose level of greater than or equal to 126 mg/dl. A prediabetic subject is someone suffering from prediabetes. A prediabetic subject is a subject with impaired fasting glucose (a fasting plasma glucose level of greater than or equal to 100 mg/dl and less than 126 mg/dl); or impaired glucose tolerance (a 2-hour plasma glucose level of ≥140 mg/dl and <200 mg/dl); or insulin resistance, resulting in an increased risk of developing diabetes. Prevention of type 2 diabetes includes treatment of prediabetes.

As used herein, the term "dyslipidemia" encompasses abnormal levels of any lipid fractions as well as specific lipoprotein abnormalities. For example, it refers to elevation of plasma cholesterol and/or elevation of triglycerides and/or elevation of free fatty acids and/or low high-density lipoprotein (HDL) level and/or high low-density lipoprotein (LDL) level and/or high very low-density lipoprotein (VLDL) level. Dyslipidemia may for example contribute to the development of atherosclerosis and ultimately symptomatic vascular disease including coronary heart disease. Dyslipidemia may or may not be associated with diabetes.

As used herein, the term "metabolic disorder" encompasses any abnormal chemical and enzymatic reactions disrupting normal metabolism due to environmental and genetic factors (environmental factors include physical activity, nutrition), leading to excessive levels or deficiency of certain substances and dysfunction of energy homeostasis. Non-limiting examples of metabolic disorders include diabetes, dyslipidemia, hypertension, being overweight, obesity, and any combination thereof.

As used herein, "AMPK-related diseases" includes pathologic or pathogenomic conditions in which the activation of AMPK provides a salutary effect. Examples of such diseases or conditions include obesity, diabetes, metabolic syndrome, acute inflammatory lung injury, heart disease, reperfusion ischemia, cancer, aging, retinal degeneration, cardiac hypertrophy, non-alcoholic fatty liver disease, hypertension, albuminuria, sporadic Alzheimer's disease, muscular dystrophy, and osteoarthritis. In addition, "AMPK-related conditions" include conditions where the activation of AMPK improves the condition associated with the primary "AMPK-related disease". For example, diabetic nephropathy (Salotto et al. (2017) J. Pharma and Expt Thera. 361:303-311) or diabetic neuropathy are "AMPK-related conditions" which may be associated with the "AMPK-related disease" of diabetes.

"Prevention" or "preventing" includes reduction of risk and/or severity of a condition, disorder, or disease.

The terms "treatment," "treating,", "treat", "attenuate" and "alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder, and include treatment of patients at risk of contracting a disease or suspected to have contracted a disease, as well as patients who are ill or have been diagnosed as suffering from a disease or medical condition. The term does not necessarily imply that a subject is treated until total recovery. These terms also refer to the maintenance and/or promotion of health in a subject not suffering from a disease but who may be susceptible to the development of an unhealthy condition. These terms are also intended to include the potentiation or otherwise enhancement of one or more primary prophylactic or therapeutic measure. The terms "treatment," "treat," "attenuate" and "alleviate" are further intended to include the dietary management of a disease or condition or the dietary management for prophylaxis or prevention a disease or condition. A treatment can be patient- or doctor-related.

Obesity, which is an excess of body fat relative to lean body mass, is a chronic disease that is highly prevalent in modern society. It is associated not only with a social stigma, but also with decreased life span and numerous medical problems, including adverse psychological development, coronary artery disease, hypertension, stroke, diabetes, hyperlipidemia, and some cancers, (see, e.g., Nishina, et al., Metab. 43:554-558, 1994; Grundy and Barnett, Dis. Mon. 36:641-731, 1990; Rissanen, et al., British Medical Journal, 301:835-837, 1990).

"Obesity related disorders" refers to those diseases or conditions where excessive body weight or high "body mass index (BMI)" has been implicated in the progression or suppression of the disease or condition. Representative examples of obesity related disorders include, without limitation diabetes, diabetic complications, insulin sensitivity, polycystic ovary disease, hyperglycemia, dyslipidemia, insulin resistance, metabolic syndrome, obesity, body weight gain, inflammatory diseases, diseases of the digestive organs, stenocardia, myocardial infarction, sequelae of stenocardia or myocardial infarction, senile dementia, and cerebrovascular dementia. See, Harrison's Principles of Internal Medicine, 13th Ed., McGraw Hill Companies Inc., New York (1994). Examples, without limitation, of inflammatory conditions include diseases of the digestive organs (such as ulcerative colitis, Crohn's disease, pancreatitis, gastritis, benign tumor of the digestive organs, digestive polyps, hereditary polyposis syndrome, colon cancer, rectal cancer, stomach cancer and ulcerous diseases of the digestive organs), stenocardia, myocardial infarction, sequelae of stenocardia or myocardial infarction, senile dementia, cerebrovascular dementia, immunological diseases and cancer in general.

The term "subject" or "individual" means any animal, including a human, that could benefit from one or more of the compounds, compositions or methods disclosed herein. Generally, the subject is a human or an avian, bovine, canine, equine, feline, hircine, lupine, murine, ovine or porcine animal. A "companion animal" is any domesticated animal, and includes, without limitation, cats, dogs, rabbits, guinea pigs, ferrets, hamsters, mice, gerbils, horses, cows, goats, sheep, donkeys, pigs, and the like. Preferably, the subject is a human or a companion animal such as a dog or cat. The term "elderly" in the context of a human means an age from birth of at least 60 years, preferably above 63 years, more preferably above 65 years, and most preferably above 70 years. The term "older adult" in the context of a human means an age from birth of at least 45 years, preferably above 50 years, more preferably above 55 years, and includes elderly subjects. For other animals, an "older adult" has exceeded 50% of the average lifespan for its particular species and/or breed within a species. An animal is considered "elderly" if it has surpassed 66% of the average expected lifespan, preferably if it has surpassed the 75% of the average expected lifespan, more preferably if it has surpassed 80% of the average expected lifespan. An elderly cat or dog has an age from birth of at least about 7 years.

As used herein, an "effective amount" is an amount that prevents a deficiency, treats a disorder, condition, or disease in a subject or, more generally, reduces symptoms, manages progression of the diseases or provides a nutritional, physiological, or medical benefit to the subject. The relative terms "improved," "increased," "enhanced" and the like refer to the effects of the composition disclosed herein relative to a composition lacking one or more ingredients and/or having a different amount of one or more ingredients, but otherwise identical.

1.5 General Terminology

As used herein, the singular forms "a," "an" and "the" include plural referents unless the context clearly dictates otherwise. Thus, for example, reference to "a component" or "the component" includes two or more components.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of recombinant DNA technology include Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth the general principles of pharmacology include Goodman and Gilman's The Pharmacological Basis of Therapeutics, 10th Ed., McGraw Hill Companies Inc., New York (2001). Standard medical terminology used herein has the meaning defined in Stedman's Medical Dictionary, 27th Edition, with veterinary medicine insert.

All percentages expressed herein are by weight of the total weight of the composition unless expressed otherwise.

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or compounds, but may also include additional features or compounds. The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the claims. Numerous specific details are set forth in the description in order to provide a thorough understanding of the present invention. The present invention may be practiced without some or all of these specific details. In other instances, well known methods and protocols have not been described in detail, in order not to unnecessarily obscure the present invention.

Compound 2, Compound 3, Compound 4 and Compound 5 activate AMPKα2β1γ1 complexes.

Compound 2 is known as 7-Methoxy-9,10-dihydrophenanthrene-2,3,5-triol.

Compound 3 is known as 2,5-Phenanthrenediol, 9,10-dihydro-, 9,10-Dihydrophenanthrene-2,5-diol, with a CAS number 1071055-42-9.

Compound 4 is known as 9,10-Dihydrophenanthrene-2, 4,7-triol, 9,10-Dihydro-2,4,7-phenanthrenetriol, 2,4,7-Trihydroxy-9,10-dihydrophenanthrene, 2,4,7-Phenanthrenetriol, 9,10-dihydro, with a CAS number 70205-52-6.

Compound 5 is known as Cannithrene 1, Cannabidihydrophenanthrene, 9,10-Dihydro-7-methoxy-3,5-phenanthrenediol, 3,5-Phenanthrenediol, 9,10-dihydro-7-methoxy, 7-Methoxy-9,10-dihydrophenanthrene-3,5-diol, with a CAS number 71135-80-3.

Figure 11:
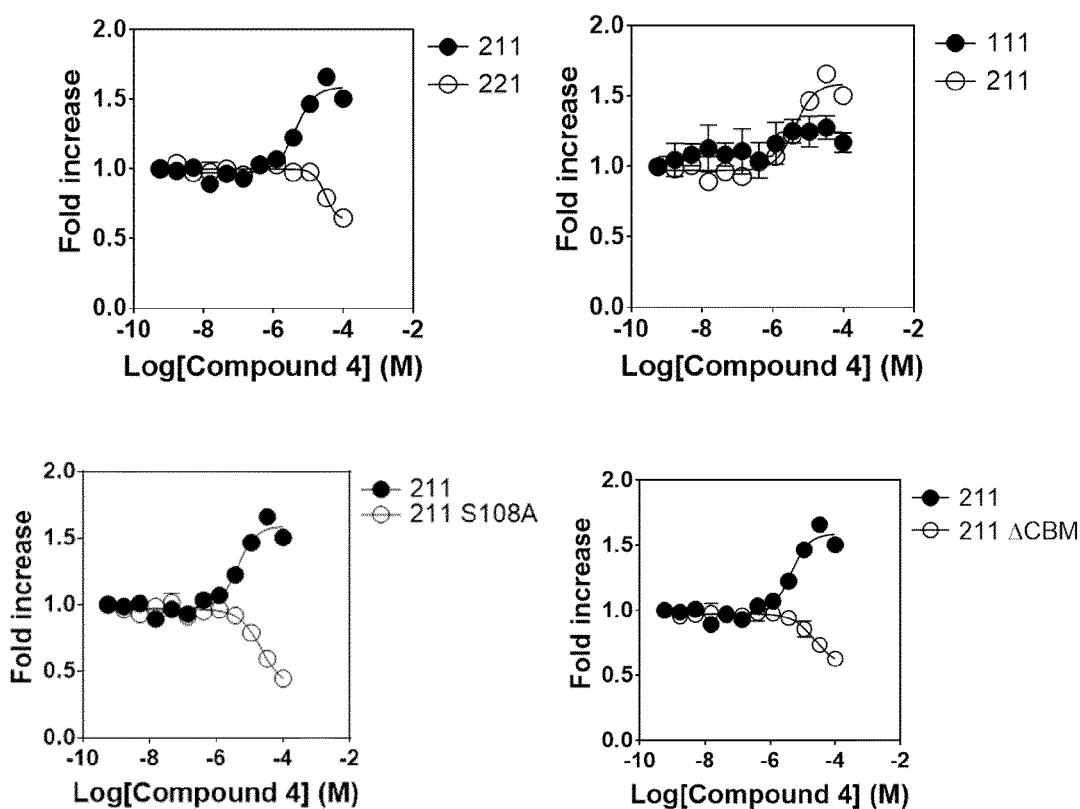

FIG. 11. Compound 4 activation of various bacterially-expressed AMPK complexes and mutants.

211 represents AMPK α2β1γ1; 221 represents AMPK α2β2γ1; 111 represents AMPK α1β1γ1;

211 S108A represents the AMPK α2β1γ1 S108A mutant;

211 ΔCBM represents the AMPK α2β1γ1 ΔCBM mutant

Compound 4 is known as 9,10-Dihydrophenanthrene-2, 4,7-triol, 9,10-Dihydro-2,4,7-phenanthrenetriol, 2,4,7-Trihydroxy-9,10-dihydrophenanthrene, 2,4,7-Phenanthrenetriol, 9,10-dihydro, with a CAS number 70205-52-6.

Compound 4 activates α1- and α2-containing complexes but does not activate β2-containing complexes, the α2β1γ1 ΔCBM mutant and AMPK complexes with the S108A mutation. Taken together, this suggests that Compound 4 activates AMPK through binding to the ADaM pocket of AMPK.

Figure 12:
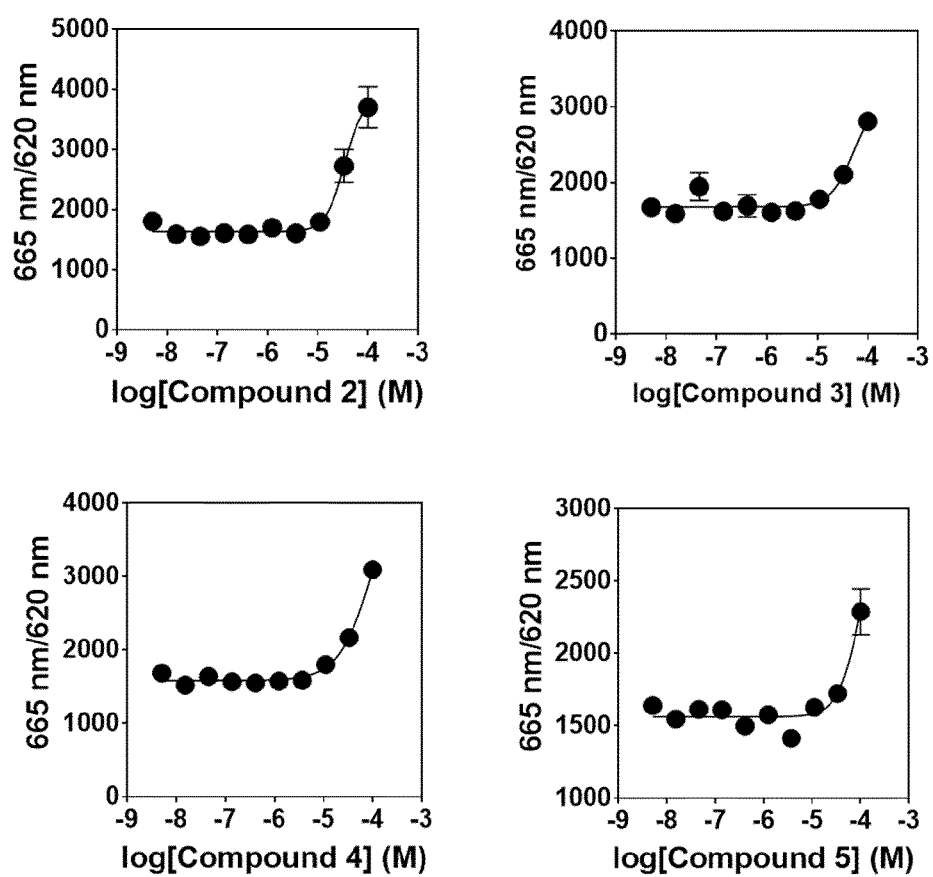

FIG. 12. Compound 2, Compound 3, Compound 4 and Compound 5 increase the phosphorylation of the AMPK substrate, acetyl-CoA carboxylase (ACC), in U2OS Flp-In T-REx mammalian cells.

Compound 2 is known as 7-Methoxy-9,10-dihydrophenanthrene-2,3,5-triol.

Compound 3 is known as 2,5-Phenanthrenediol, 9,10-dihydro-, 9,10-Dihydrophenanthrene-2,5-diol, with a CAS number 1071055-42-9.

Compound 4 is known as 9,10-Dihydrophenanthrene-2,4,7-triol, 9,10-Dihydro-2,4,7-phenanthrenetriol, 2,4,7-Trihydroxy-9,10-dihydrophenanthrene, 2,4,7-Phenanthrenetriol, 9,10-dihydro, with a CAS number 70205-52-6.

Compound 5 is known as Cannithrene 1, Cannabidihydrophenanthrene, 9,10-Dihydro-7-methoxy-3,5-phenanthrenediol, 3,5-Phenanthrenediol, 9,10-dihydro-7-methoxy, 7-Methoxy-9,10-dihydrophenanthrene-3,5-diol, with a CAS number 71135-80-3.

Figure 13:
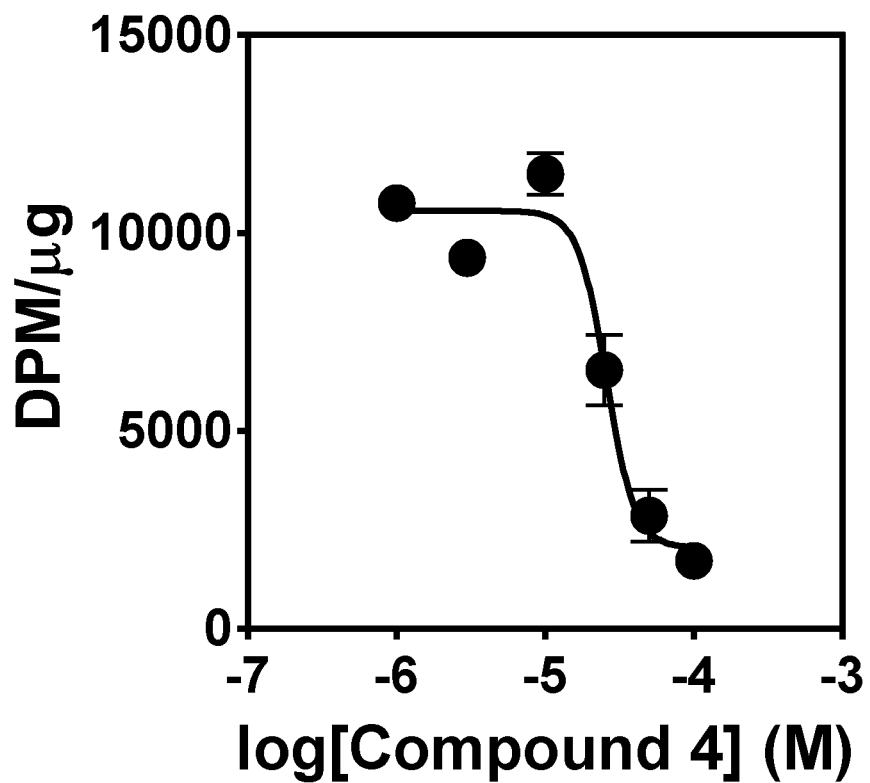

FIG. 13. Compound 4 displays a dose-dependent inhibition of lipogenesis in primary hepatocytes.

Compound 4 is known as 9,10-Dihydrophenanthrene-2,4,7-triol, 9,10-Dihydro-2,4,7-phenanthrenetriol, 2,4,7-Trihydroxy-9,10-dihydrophenanthrene, 2,4,7-Phenanthrenetriol, 9,10-dihydro, with a CAS number 70205-52-6.

Figure 14:
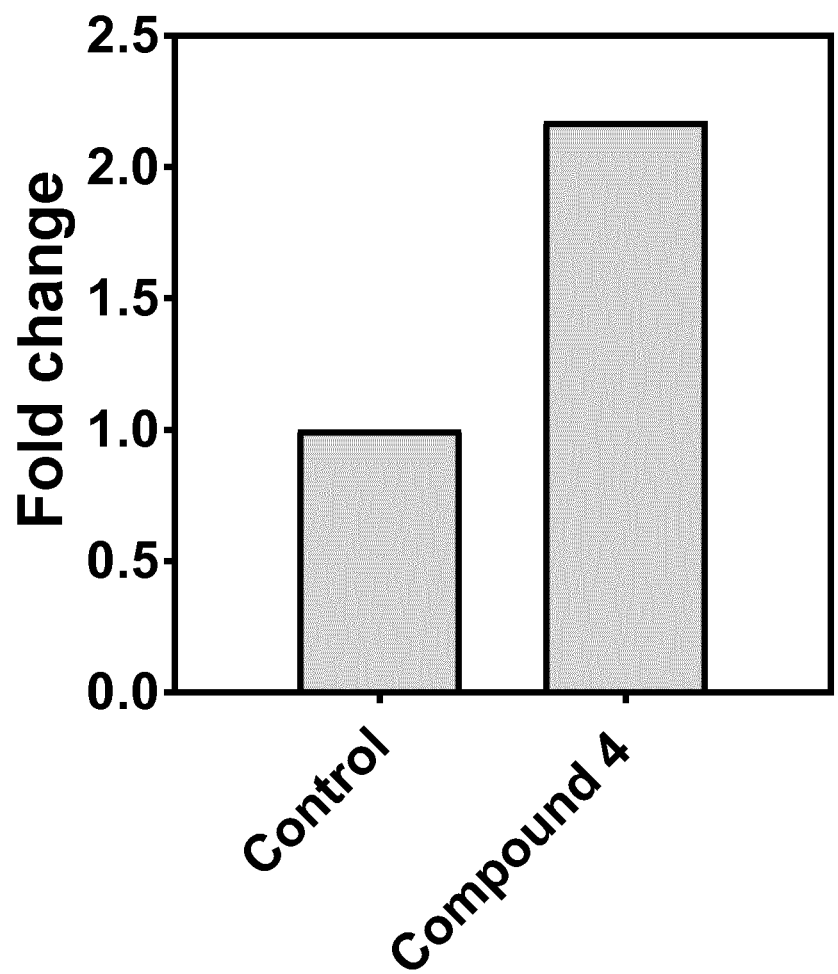

FIG. 14. Compound 4 increases glucose uptake into differentiated C2C12 cells.

Compound 4 is known as 9,10-Dihydrophenanthrene-2,4,7-triol, 9,10-Dihydro-2,4,7-phenanthrenetriol, 2,4,7-Trihydroxy-9,10-dihydrophenanthrene, 2,4,7-Phenanthrenetriol, 9,10-dihydro, with a CAS number 70205-52-6.

Figure 15:
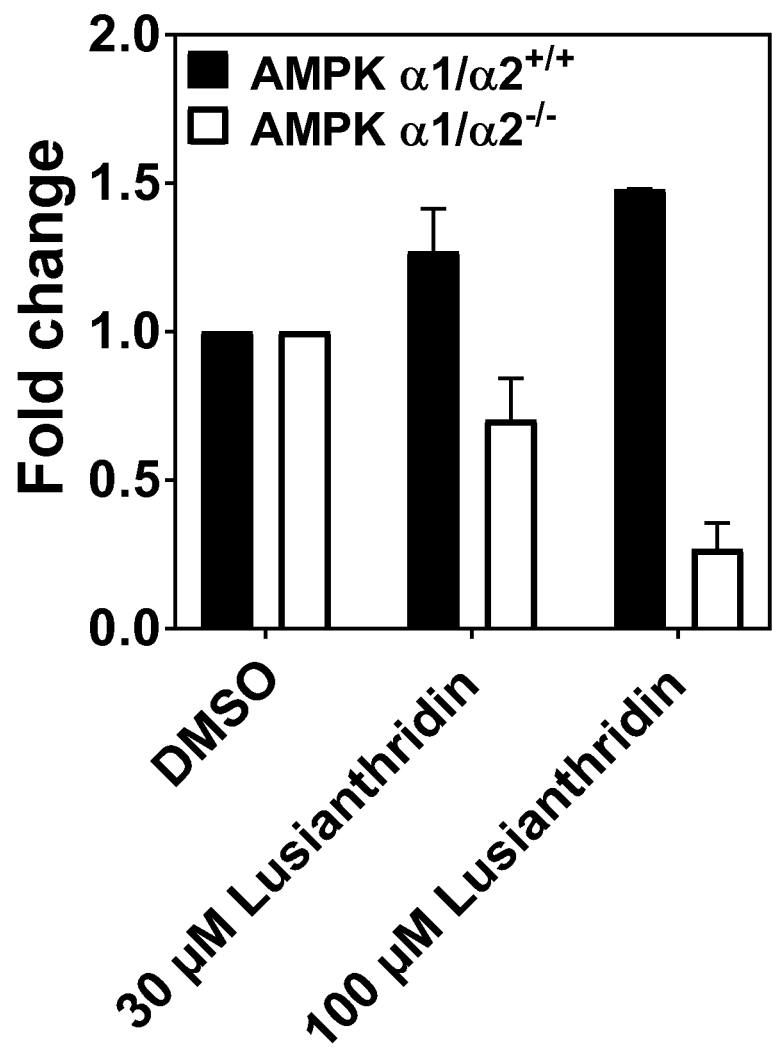

FIG. 15. Lusianthridin does not increase glucose uptake in C2C12 lacking the AMPKα1/α2 subunits.

Figure 16:
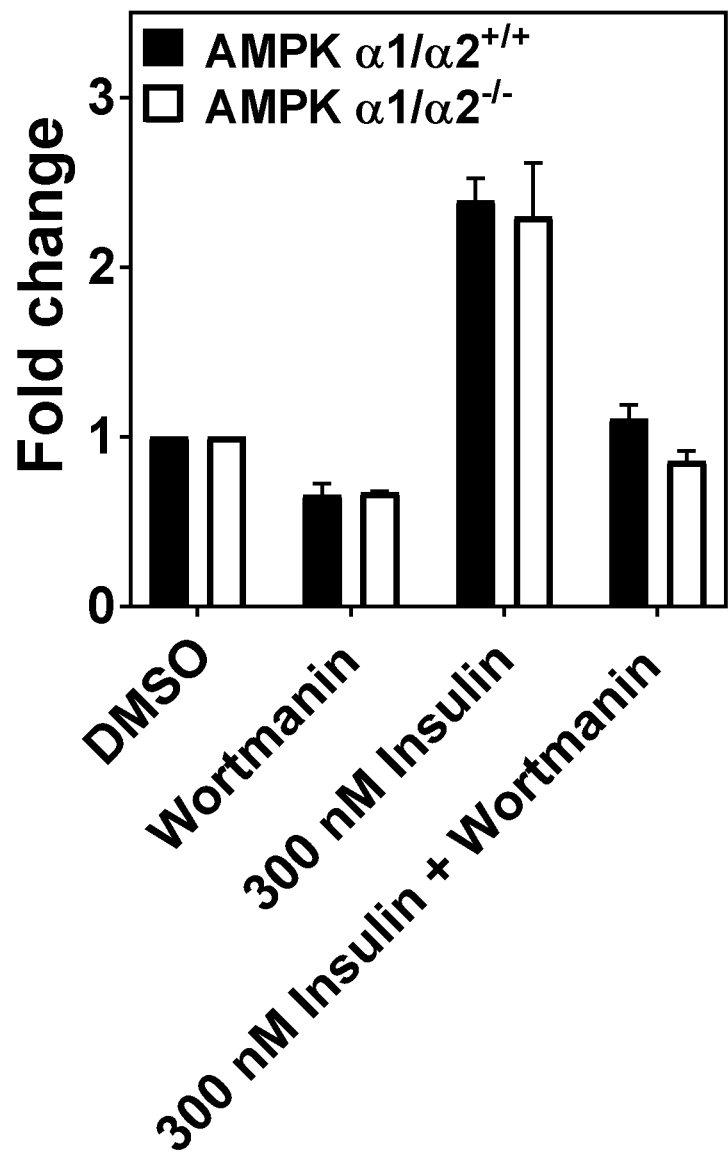

FIG. 16. Insulin can increase glucose uptake in C2C12 lacking the AMPKα1/α2 subunits.

Figure 17:
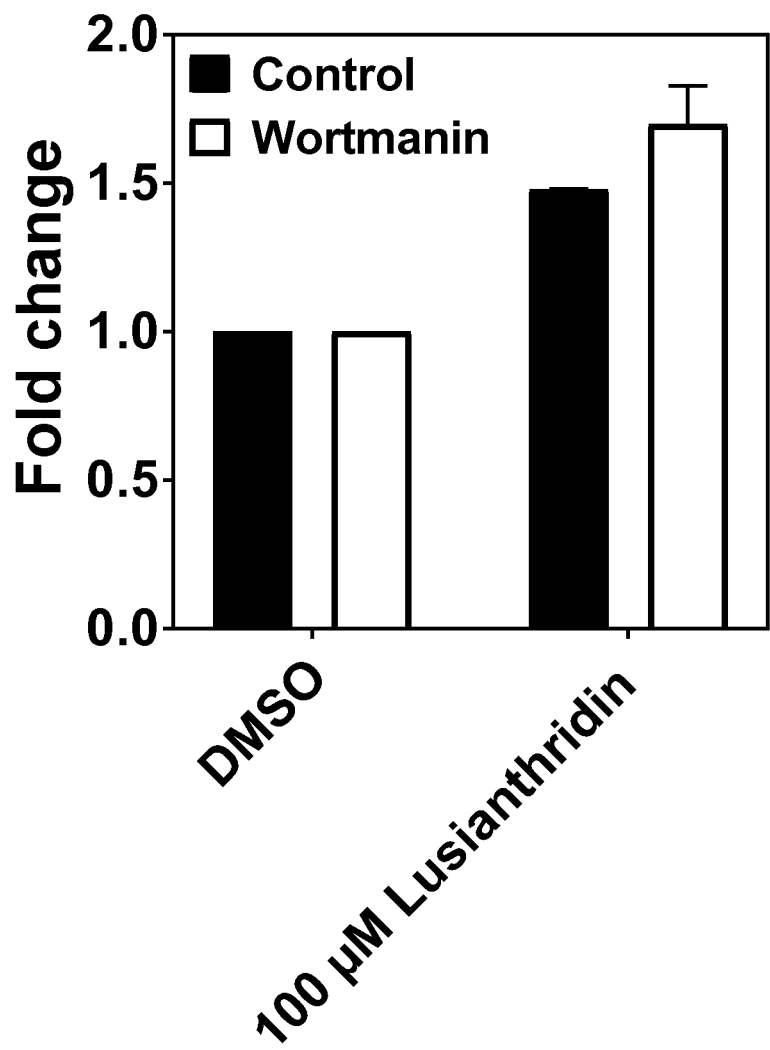

FIG. 17. Wortmanin does not affect Lusianthridin-stimulated glucose uptake in C2C12.

Figure 18:
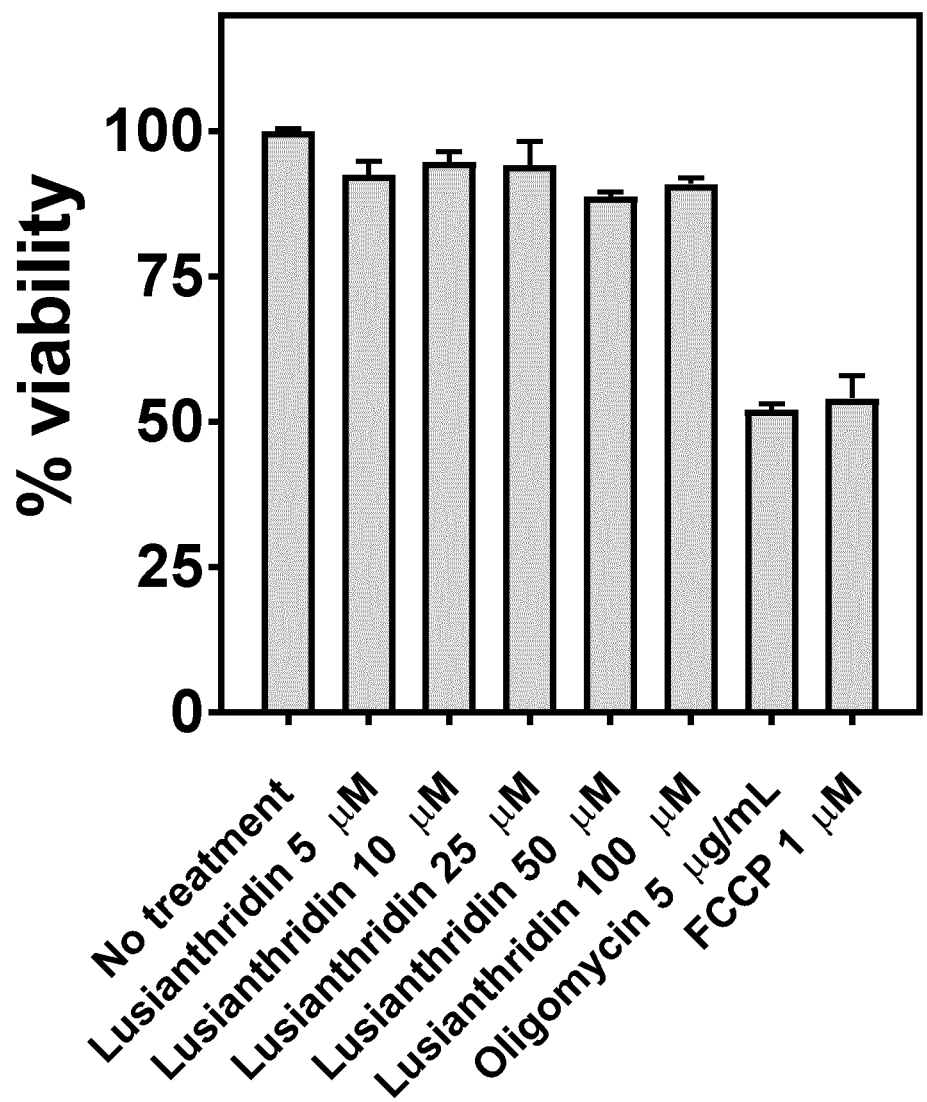

FIG. 18. Lusianthridin did not display a cytotoxic effect on mouse primary hepatocytes.

Mouse primary hepatocytes were treated with the indicated concentrations of Lusianthridin, Oligomycin and FCCP for 1 h at 37 C. Cell viability was determined by using an MTT assay as per the manufacturer's protocol. The results are displayed as the percentage of viable cells after treatment with these compounds.

Figure 19:
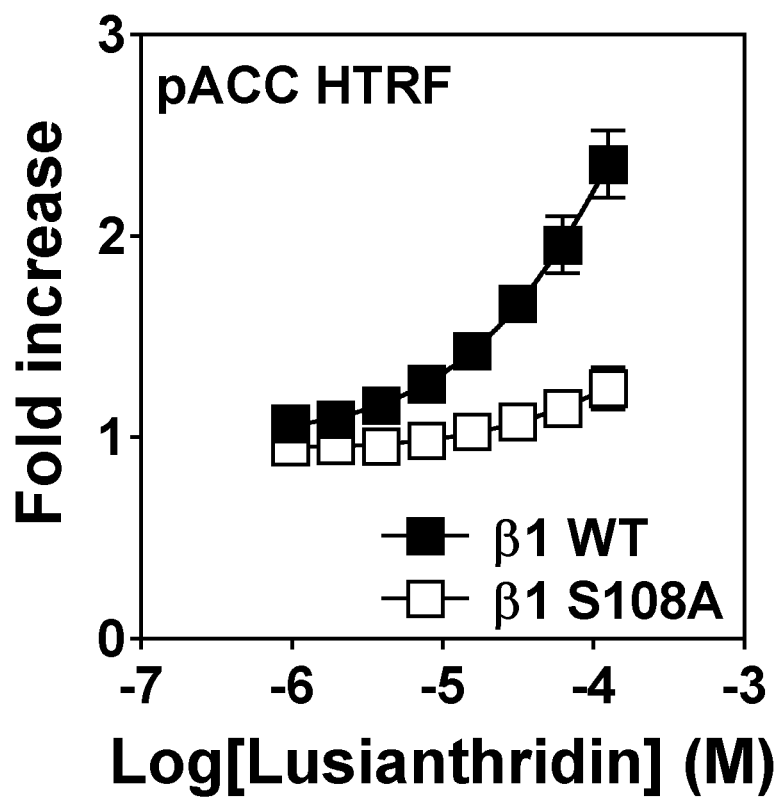

FIG. 19. Lusianthridin does not activate AMPK in cells stably expressing an ADaM-binding site AMPK mutant (β1 S108A) as assessed by the pACC HTRF assay.

The β1 WT and β1 S108A mutant were stably expressed in AMPKβ1β2 double knockout cells and treated with varying concentrations of Lusianthridin for 30 mins at 37 C. Lusianthridin did not increase pACC in cells expressing the β1 S108A mutant. In contrast, Lusianthridin was capable of activating the β1 WT-expressing cells.

Figure 20:
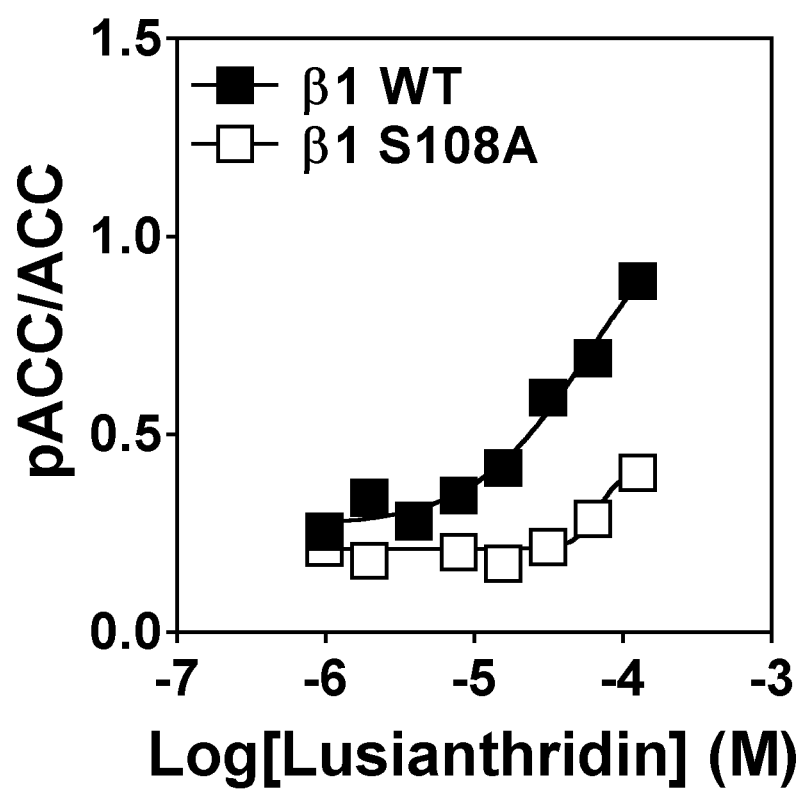

FIG. 20. Lusianthridin does not activate AMPK in cells stably expressing an ADaM-binding site AMPK mutant (β1 S108A) as assessed by western blot analysis.

In contrast to β1 WT-expressing cells, Lusianthridin did not increase phosphorylation of ACC in cells expressing the β1 S108A mutant-expressing cells. Taken together, this demonstrates that the ability of Lusianthridin to activate AMPK in cells is through its ability to bind to the ADaM site and not the nucleotide-binding site of AMPK.

EXAMPLES

Example 1

Chemical Synthesis of Lusianthridin by Wittig Reaction Between (3-(benzyloxy)-5-methoxybenzyl)triphenylphosphonium bromide and 5-(benzyloxy)-2-iodobenzaldehyde Part 1: Synthesis of (3-(benzyloxy)-5-methoxybenzyl) triphenylphosphonium bromide.

After suitable protection, 3,5-dihydroxybenzoic acid methyl ester was reduced to a primary alcohol, and converted to its corresponding alkyl halide before reaction with triphenylphosphine to give the desired triphenylphosphonium ylide reagent (Scheme 1).

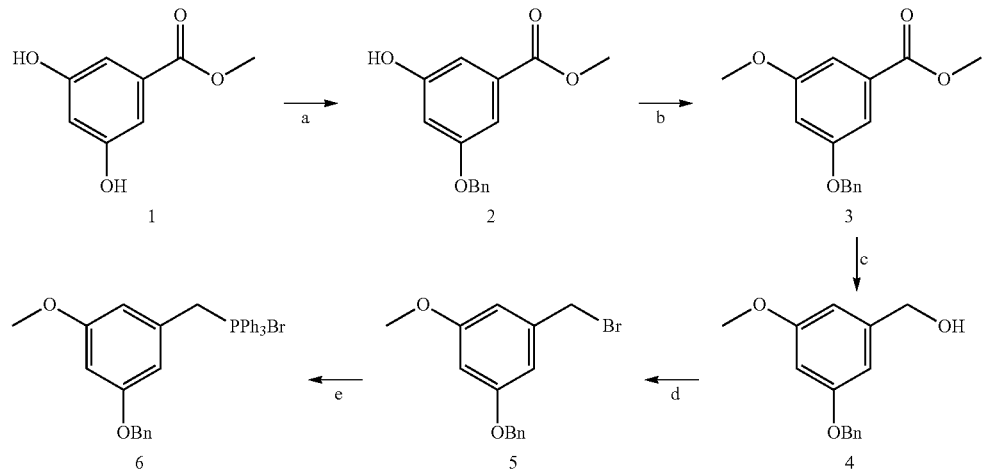

Scheme 1: Synthesis of (3-(benzyloxy)-5-methoxybenzyl)triphenylphosphonium bromide.

Reagents and conditions: (a) K$_2$CO$_3$, BnBr, Acetone, 60° C., 31%; (b) K$_2$CO$_3$, MeI, Acetone, rt, 94%; (c) LAH, THF, rt, 92%; (d) PBr$_3$, 1,4-dioxane, 40° C., 80%; (e) PPh$_3$, Toluene, 100° C., 82%.

Step a. To a solution of methyl 3,5-dihydroxybenzoate 1 (300 g, 1784.12 mmol) in acetone (7200 mL) was added potassium carbonate (271.22 g, 1962.53 mmol). The suspension was stirred at room temperature for 10 min. Benzyl bromide (222.50 mL, 1873.32 mmol) was added, and the resultant suspension was heated at 60° C. for 12 h. After cooling to room temperature, the suspension was filtered, the filter cake washed with acetone, and the filtrate was concentrated to a residue. The residue was purified by automated normal-phase chromatography and eluted with ethyl acetate/hexanes to give methyl 3-(benzyloxy)-5-hydroxybenzoate 2 as an off-white solid. (144 g, 31% yield). 1H NMR (300 MHz, DMSO-d6) δ ppm: 9.89 (s, 1H), 7.33-7.46 (m, 5H), 7.01 (dd, J=6.30, 0.90 Hz, 2H), 6.67 (t, J=2.40 Hz, 1H), 5.11 (s, 2H), 3.82 (s, 3H); MS (ES+) m/z 257.1 [M−H]+; HPLC-UV analysis: retention time=13.35 min; detection: 190-400 nm: peak area, 99.81%; eluent A, 0.1% TFA in water; eluent B, Acetonitrile; isocratic/gradient over 30 min with a flow rate of 1.0 mL min−1.

Step b. To a solution of methyl 3-(benzyloxy)-5-hydroxybenzoate 2 (140 g, 542.06 mmol) in acetone (7000 mL) was added potassium carbonate (224.74 g, 1626.20 mmol). The suspension was stirred at room temperature for 10 min. Iodomethane (168.73 mL, 2710.34 mmol) was added, and the resultant suspension was stirred at room temperature for 16 h. The suspension was filtered, the filter cake washed with acetone, and the filtrate was concentrated to a residue. The residue was purified by automated normal-phase chromatography and eluted with ethyl acetate/hexanes to give methyl 3-(benzyloxy)-5-methoxybenzoate 3 as liquid. (125 g, 94% yield). 1H NMR (300 MHz, DMSO-d6) δ ppm: 7.33-7.48 (m, 6H), 7.16 (t, J=2.10 Hz, 1H), 7.08 (d, J=1.20 Hz, 1H), 6.87 (t, J=2.40 Hz, 1H), 5.15 (s, 2H), 3.84 (s, 3H), 3.79 (s, 3H); MS (ES+) m/z 273.1 [M+H]+; HPLC-UV analysis: retention time=15.31 min; detection: 190-400 nm: peak area, 99.78%; eluent A, 0.1% TFA in water; eluent B, Acetonitrile; isocratic/gradient over 30 min with a flow rate of 1.0 mL min−1.

Step c. Lithium aluminium hydride (16.86 g, 444.36 mmol) in THF (605 mL) was added to methyl 3-(benzyloxy)-5-methoxybenzoate 3 (121 g, 444.36 mmol) in THF (1600 mL) at 0° C. The suspension was stirred at 0° C. for 20 min, at room temperature for 1 h. The reaction mixture was diluted with THF and quenched by addition of water. The resultant mixture was filtered through a pad of celite, and washed with ethyl acetate. The filtrate was concentrated in vacuo to give (3-(benzyloxy)-5-methoxyphenyl)methanol 4 as liquid. (100 g, 92% yield). 1H NMR (300 MHz, DMSO-d6) δ ppm: 7.30-7.46 (m, 5H), 6.59 (d, J=0.60 Hz, 1H), 6.51 (s, 1H), 6.45 (d, J=2.40 Hz, 1H), 5.19 (t, J=5.70 Hz, 1H), 5.07 (s, 2H), 4.44 (d, J=5.70 Hz, 2H), 3.72 (s, 3H); MS (ES+) m/z 245.1 [M+H]+; HPLC-UV analysis: retention time=12.86 min; detection: 190-400 nm: peak area, 99.64%; eluent A, 0.1% TFA in water; eluent B, Acetonitrile; isocratic/gradient over 30 min with a flow rate of 1.0 mL min−1.

Step d. To a solution of (3-(benzyloxy)-5-methoxyphenyl) methanol 4 (100 g, 409.34 mmol) in 1,4-dioxane (1000 mL) was added phosphorous tribromide (50.54 mL, 532.15 mmol). The reaction mixture was stirred at 40° C. for 1 h and quenched by addition of water. The aqueous phase was extracted with ethyl acetate, and the combined organic extracts were washed with water, brine and concentrated to give 1-(benzyloxy)-3-(bromomethyl)-5-methoxybenzene 5 as pale yellow solid. (100 g, 80% yield). 1H NMR (300 MHz, DMSO-d6) δ ppm: 7.33-7.46 (m, 5H), 6.72 (s, 1H), 6.63 (s, 1H), 6.54 (d, J=1.80 Hz, 1H), 5.09 (d, J=5.40 Hz, 2H), 4.62 (d, J=5.70 Hz, 2H), 3.74 (s, 3H); MS (ES+) m/z 309 [M+2H]+; HPLC-UV analysis: retention time=15.77 min; detection: 190-400 nm: peak area, 99.71%; eluent A, 0.1% TFA in water; eluent B, Acetonitrile; isocratic/gradient over 30 min with a flow rate of 1.0 mL min−1.

Step e. To a solution of 1-(benzyloxy)-3-(bromomethyl)-5-methoxybenzene 5 (100 g, 325.53 mmol) in toluene (2488 mL) was added triphenylphosphine (85.38 g, 325.53 mmol). The reaction mixture was stirred at 100° C. for 6 h, then allowed to cool to room temperature. The solid was collected by filtration, washed with ether, and dried under vacuum to give (3-(benzyloxy)-5-methoxybenzyl)triphenylphosphonium bromide 6 as an off-white solid. (150 g, 82% yield). 1H NMR (400 MHz, DMSO-d6) δ ppm: 7.89-7.91 (m, 3H), 7.65-7.75 (m, 12H), 7.28-7.37 (m, 5H), 6.51 (s, 1H), 6.23 (s, 1H), 6.12 (s, 1H) 5.07 (d, J=15.60 Hz, 2H), 4.82 (s, 2H), 3.48 (s, 3H); MS (ES+) m/z 489.2 [M−HBr]+; HPLC-UV analysis: retention time=14.19 min; detection: 190-400 nm: peak area, 95.51%; eluent A, 0.1% TFA in water; eluent B, Acetonitrile; isocratic/gradient over 30 min with a flow rate of 1.0 mL min−1.

Part 2: Synthesis of 5-(benzyloxy)-2-iodobenzaldehyde

3-Hydroxybenzaldehyde was protected before ortho iodination, as displayed in Scheme 2.

Scheme 2: Synthesis of 5-(benzyloxy)-2-iodobenzaldehyde.

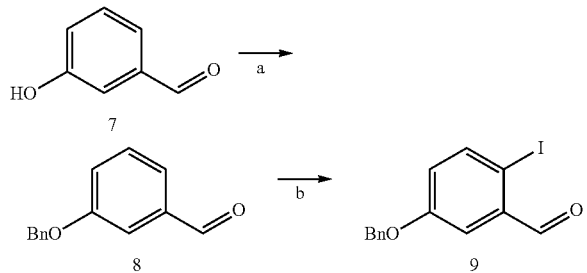

Reagents and conditions: (a) K$_2$CO$_3$, BnBr, Acetone, 60° C., 96%;
(b) CF$_3$COOAg, I$_2$, CHCl$_3$, rt, 59%;

Step a. To a solution of 3-hydroxybenzaldehyde 7 (25 g, 204.85 mmol) in acetone (250 mL) was added potassium carbonate (42.46 g, 307.27 mmol). The suspension was stirred at room temperature for 10 min. Benzyl bromide (31.38 mL, 264.25 mmol) was added, and the resultant suspension was heated at 60° C. for 12 h. After cooling to room temperature, the suspension was filtered, the filter cake washed with acetone, and filtrate concentrated to a residue. The residue was purified by automated normal-phase chromatography and eluted with ethyl acetate/hexanes to give 3-(benzyloxy)benzaldehyde 8 as an off-white solid. (42 g, 96% yield). 1H NMR (400 MHz, DMSO-d6) δ ppm: 9.98 (s, 1H), 7.27-7.50 (m, 5H), 7.25-7.26 (m, 2H), 5.14 (s, 2H); GCMS: m/z 212.1: (GCMS condition: column: HP-5 (30 m×320 μm×0.25 μm); gradient:120° C.-300° C., 40° C. min−1; HPLC-UV analysis: retention time=14.37 min; detection: 190-400 nm: peak area, 99.58%; eluent A, 0.1% TFA in water; eluent B, Acetonitrile; isocratic/gradient over 30 min with a flow rate of 1.0 mL min−1.

Step b. To a solution of 3-(benzyloxy)benzaldehyde 8 (42 g, 197.87 mmol) in chloroform (1050 mL) was added Silver trifluoroacetate (65.56 g, 296.81 mmol). The suspension was stirred at 0° C. for 10 min. Iodine (32.43 g, 126.90 mmol) was added at 0° C. and the resultant suspension was stirred at room temperature for 12 h and quenched by addition of water. The resultant mixture was filtered through a pad of celite, washed with dichloromethane. The aqueous phase was extracted dichloromethane, and the combined organic extracts were washed with water, brine and concentrated to a residue. The residue was purified by automated normal-phase chromatography and eluted with ethyl acetate/hexanes to give 5-(benzyloxy)-2-iodobenzaldehyde 9 as an off-white solid. (40 g, 59% yield). 1H NMR (400 MHz, CDCl3) δ ppm: 10.04 (s, 1H), 7.83 (d, J=8.40 Hz, 1H), 7.54 (s, 1H), 7.37-7.53 (m, 5H), 7.01 (dd, J=8.80, 3.20 Hz, 1H), 5.12 (s, 2H); GCMS m/z 338: (GCMS condition: column: ZB1MS (10 m×100 μm×0.1 μm); gradient:120° C.-300° C., 40° C. min−1.; HPLC-UV analysis: retention time=16.04 min; detection: 190-400 nm: peak area, 99.84%; eluent A, 0.1% TFA in water; eluent B, Acetonitrile; isocratic/gradient over 30 min with a flow rate of 1.0 mL min−1.

Part 3: Synthesis of Lusianthridin.

Lusianthridin was prepared through a Wittig reaction between (3-(benzyloxy)-5-methoxybenzyl)triphenylphosphonium bromide and 5-(benzyloxy)-2-iodobenzaldehyde, followed by cyclization, deprotection, and reduction, as shown in Scheme 3.

Step b. To a solution of (Z)-4-(benzyloxy)-2-(3-(benzyloxy)-5-methoxystyryl)-1-iodobenzene 10 (50 g, 91.17 mmol) in toluene (1250 mL) was added tributyltin hydride (49.14 mL, 182.34 mmol) and azobisisobutyronitrile (7.48 g, 45.58 mmol). The reaction mixture was sparged with nitrogen for 5 min and heated at 100° C. for 16 h. The reaction mixture was concentrated to a residue and the residue was purified by automated normal-phase chromatography and eluted with ethyl acetate/hexanes to give 1:1 mixture of 4,7-bis(benzyloxy)-2-methoxyphenanthrene 11a and 2,7-bis(benzyloxy)-4-methoxyphenanthrene 11b as an off-white solid. (25 g, 65% yield). MS (ES+) m/z 421.3 [M+H]+; HPLC-UV analysis: retention time=(6.59 & 6.70)

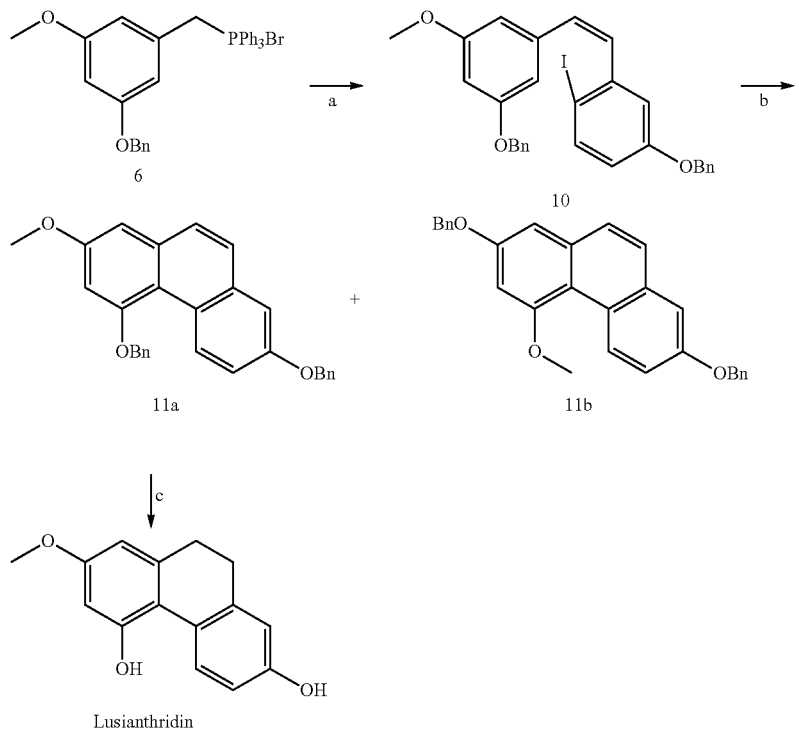

Scheme 3: Synthesis of lusianthridin.

Reagents and conditions: (a) KOtBu, 5-(benzyloxy)-2-iodobenzaldehyde, THF, rt, 86%; (b) Bu₃SnH, AIBN, Toluene, 100° C., 65%; (c) Pd/C, AcOH, THF, Hydrogen balloon, rt, then SFC Step a. To a solution of 5-(benzyloxy)-2-iodobenzaldehyde 9 (36 g, 106.46 mmol) in THF (3600 mL) was added (3-(benzyloxy)-5-methoxybenzyl)triphenylphosphonium bromide 6 (127.32 g, 223.57 mmol). The suspension was stirred at 0° C. Potassium tert-butoxide (26.28 g, 234.08 mmol) was added at 0° C. and the resultant suspension was stirred at room temperature for 12 h. The reaction mixture was concentrated to a residue and the residue was purified by automated normal-phase chromatography and eluted with ethyl acetate/hexanes to give (Z)-4-(benzyloxy)-2-(3-(benzyloxy)-5-methoxystyryl)-1-iodobenzene 10 as an off-white solid. (50 g, 86% yield). 1H NMR (400 MHz, CDCl3) δ ppm: 7.74 (d, J=8.80 Hz, 1H), 7.26-7.42 (m, 8H), 6.89 (d, J=3.20 Hz, 1H), 6.49-6.65 (m, 4H), 6.40 (s, 3H), 6.33 (t, J=1.60 Hz, 1H), 4.85 (s, 4H), 3.62 (s, 3H); MS (ES+) m/z 549.1 [M+H]+; HPLC-UV analysis: retention time=18.74 min; detection: 190-400 nm: peak area, 89.98%; eluent A, 0.1% TFA in water; eluent B, Acetonitrile; isocratic/gradient over 30 min with a flow rate of 1.0 mL min−1.

min; detection: 190-400 nm: peak area, 99.28%; eluent A, 0.1% TFA in water; eluent B, 0.1% TFA in Acetonitrile; isocratic/gradient over 10 min with a flow rate of 2.0 mL min−1.

Step c. To a solution of 4,7-bis(benzyloxy)-2-methoxyphenanthrene 11a and 2,7-bis(benzyloxy)-4-methoxyphenanthrene 11b (25 g, 59.45 mmol) in acetic acid (2000 mL) and THF (250 mL) was added 10% Pd/C (25 g). The reaction mixture was stirred at room temperature 2 days under hydrogen balloon. The resultant mixture was filtered through a pad of Celite, washed with ethyl acetate and the filtrate was concentrated to give a 1:1 mixture of regioisomers. (11.50 g, 79% yield). This crude product (11.50 g, 1:1 mixture) was purified by SFC (SFC condition: column: YMC Amylose-C; detection: 210 nm: co-solvent: 0.5% isopropyl amine in methanol; flow rate of 4.0 mL min−1) to give 7-methoxy-9,10-dihydrophenanthrene-2,5-diol Lusianthridin as an off white solid (1.1 g). 1H NMR (400 MHz, DMSO-d6) δ ppm: 9.60 (s, 1H), 9.18 (s, 1H), 8.08 (d, J=8.80 Hz, 1H), 6.60 (s, 1H), 6.59 (d, J=7.20 Hz, 1H), 6.37 (s, 1H), 6.32 (s, 1H), 3.70 (s, 3H), 2.60 (s, 4H); 13C NMR (100 MHz, DMSO-d6) δ ppm: 158.13, 155.52, 155.45, 140.32, 138.86, 129.05, 124.67, 114.86, 114.62, 113.09, 105.15, 100.97, 55.25, 30.70, 29.95; MS (ES+) m/z 243.1 [M+H]+; Elemental analysis calculated (%) for C15H14O3+ 0.2CH3OH: C73.41, H 6.00. Found: C73.43, H 5.84; HPLC-UV analysis: retention time=11.84 min; detection: 190-400 nm: peak area, 98.62%; eluent A, 0.1% TFA in water; eluent B, Acetonitrile; isocratic/gradient over 30 min with a flow rate of 1.0 mL min−1.

Example 2

Lusianthridin Activates Bacterially-Expressed AMPKα2β1γ1 and α1β1γ1 Complexes in a Dose-Dependent Manner.

Lusianthridin (CAS 87530-30-1) was isolated from Thunia alba fruit. It was sourced from Analyticon (NP-012362). The plant was purchased through Analyticon's biomaterial supplier in 2003. The country of origin is Nepal. The AMPK heterotrimers were expressed in bacteria and purified through the His-α subunit by nickel purification. AMPK complexes were purified through gel filtration and phosphorylated by incubation with CaMKKβ, and further purified with a final gel filtration purification step. Phosphorylated purified AMPK was incubated with varying concentrations of ligand for 30 mins using substrate and reagents from the HTRF-KinEASE Cisbio assay kit (STK S1 Kit). Phosphorylation of the substrate was measured by incubating with donor and acceptor antibodies for 2 h at room temperature as per the manufacturer's protocol (and Coulerie et al., (2016) PMID: 27792327) and phosphorylated peptide detected by performing HTRF. The 665 nm/620 nm ratio was determined and the results are plotted as fold activation compared to the respective AMPK complex without any compound.

FIGS. 1 to 5 show that Lusianthridin (7-Methoxy-9,10-dihydrophenanthrene-2,5-diol, CAS number 87530-30-1) does not activate AMPK complexes containing the β2-subunit.

Furthermore, it does not activate AMPK complexes with a mutation in the β1 subunit (S108A) or a deletion of the carbohydrate-binding module (ΔCBM). This activation profile is characteristic of activators mediating their effects through the ADaM (allosteric drug and metabolic) site. The AMPK γ1 R298G mutant which shows impaired AMP regulation has no effect on activation by Lusianthridin. These data are consistent with Lusianthridin activation at the ADaM binding pocket of AMPK formed between the kinase domain of the a subunit and the CBM of the β subunit.

Example 3

Lusianthridin Increases the Phosphorylation of the AMPK Substrate, acetyl-CoA carboxylase (ACC), in U2OS Flp-In T-REx Mammalian Cells.

U2OS Flp-In T-REx cells were seeded at 100 K in a 96-well plate and left overnight at 37 C in DMEM GlutaMAX (Thermo Fisher Scientific) supplemented with 10% (vol/vol) FBS and 100 U/ml penicillin G, and 100 μg/ml streptomycin. Cells were treated for 1 h with varying concentrations of Lusianthridin in media lacking FBS and then cells were lysed in 50 μl of Cisbio lysis buffer #1 supplemented with blocking solution as per the manufacturer's protocol (Cisbio). Cells were lysed for 30 mins at room temperature before 16 μl of lysate was incubated with 4 μl of the HTRF antibodies (1:40 dilution of the acceptor and donor (p)ACC antibodies, as per the manufacturers protocol). Lysates were incubated overnight with the antibodies before 665 nm/620 nm ratio was determined using a MolecularDevices i3 plate reader (with a HTRF cartridge add-on). For western blot analysis, SDS-sample buffer was added to the remainder of the lysate, denatured at 95 C and then subjected to western blot analysis with phospho-specific and total ACC antibodies (Cell Signalling). Bands were visualized by incubating with Li-Cor secondary antibody and scanned on a Li-Cor Odyssey machine.

Figure 1:
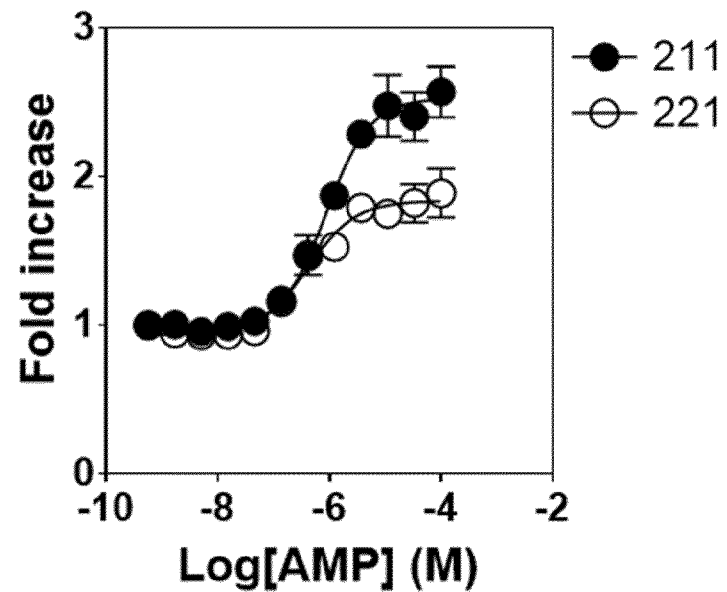
FIG. 1. AMP and Lusianthridin activation of bacterially-expressed AMPKα2β1γ1 (211) or α2β2γ1 (221) complexes. Lusianthridin (7-Methoxy-9,10-dihydrophenanthrene-2,5-diol, CAS number 87530-30-1) does not activate β2-containing complexes. It has been previously reported that activators at the Allosteric Drug and Metabolic (ADaM) binding site in AMPK, have weaker activation of β2-containing AMPK complexes. In contrast, regulators at the AMP-binding site are not influenced by the β-iso form composition of AMPK.
Figure 1:
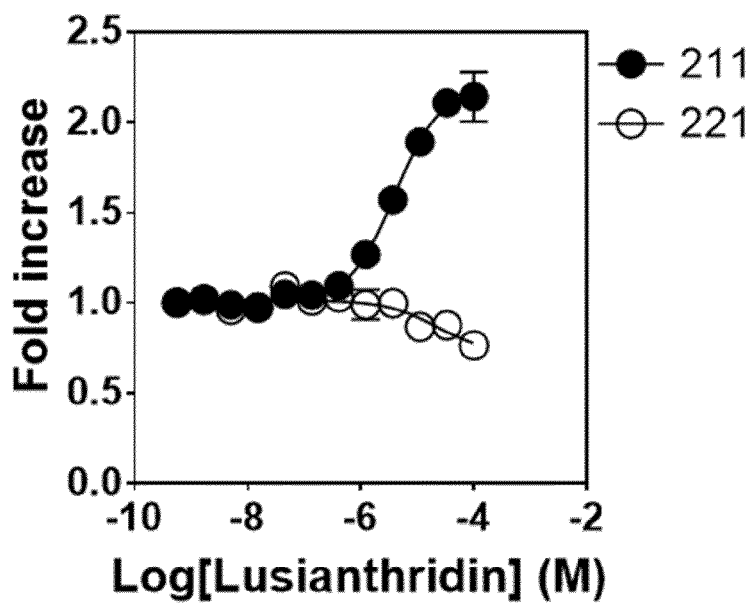
Figure 2:
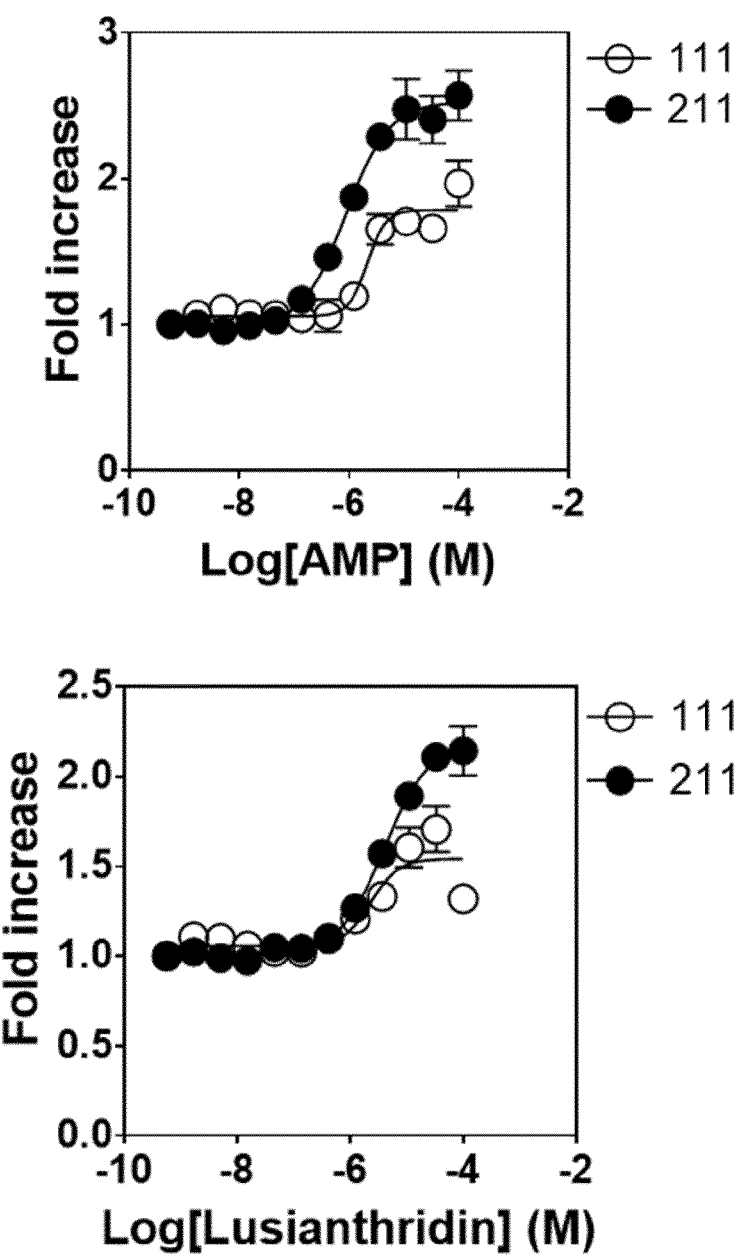
FIG. 2. AMP and Lusianthridin activation of bacterially-expressed AMPKα1β1γ1 (111) or α2β1γ1 (211) complexes. Lusianthridin activates α1- and α2-containing complexes.
Figure 3:
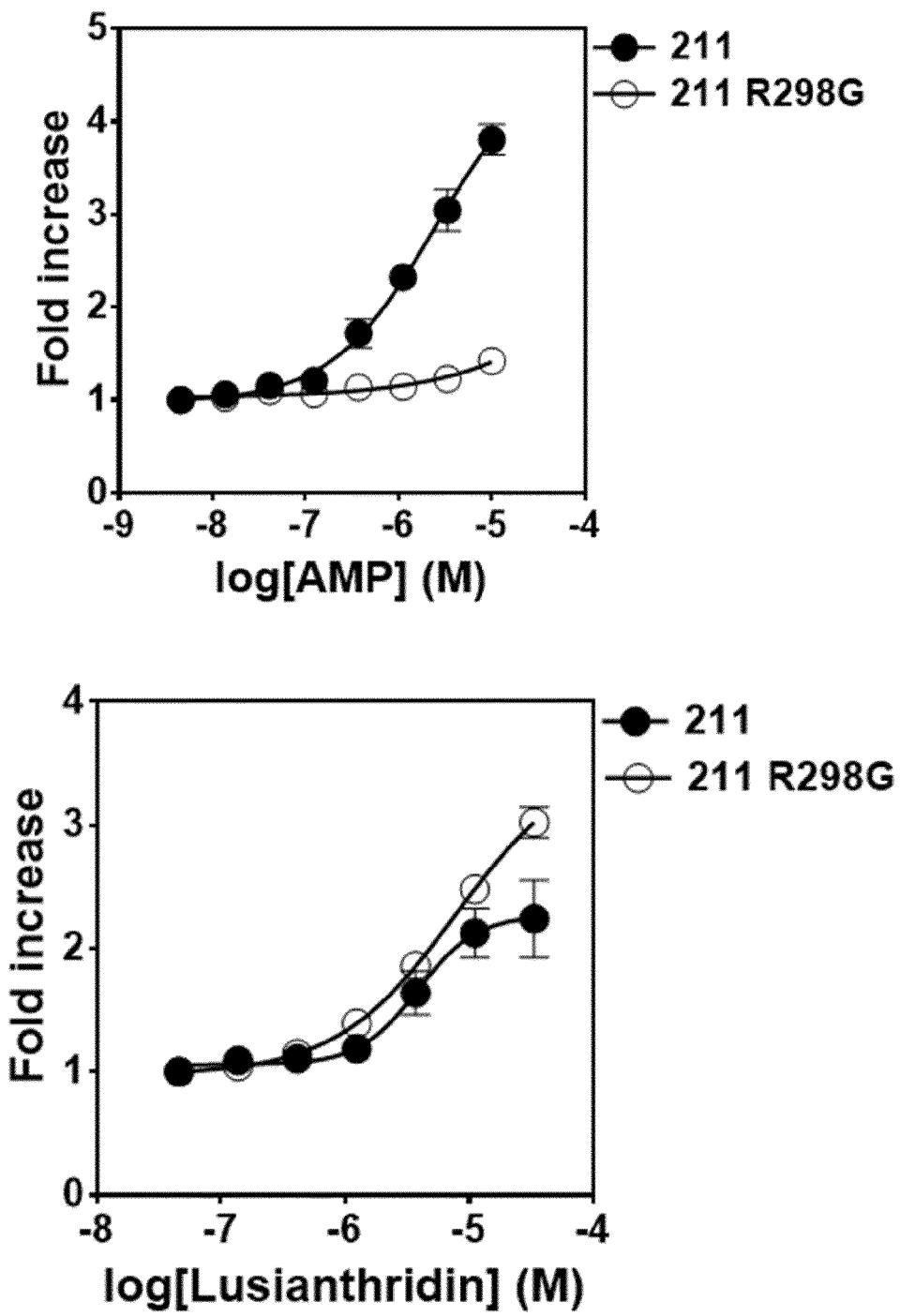
FIG. 3. AMP and Lusianthridin activation of bacterially-expressed AMPKα2β1γ1 (211) or α2β1γ1γ1R298G (211 R298G) mutant complexes. Lusianthridin still activates AMPK complexes harbouring a mutation in the γ1 AMP binding pocket. In contrast, AMP regulation of this mutant is impaired. This suggests that Lusianthridin does not activate AMPK through the nucleotide-binding sites in the AMPKγ subunit.
Figure 4:
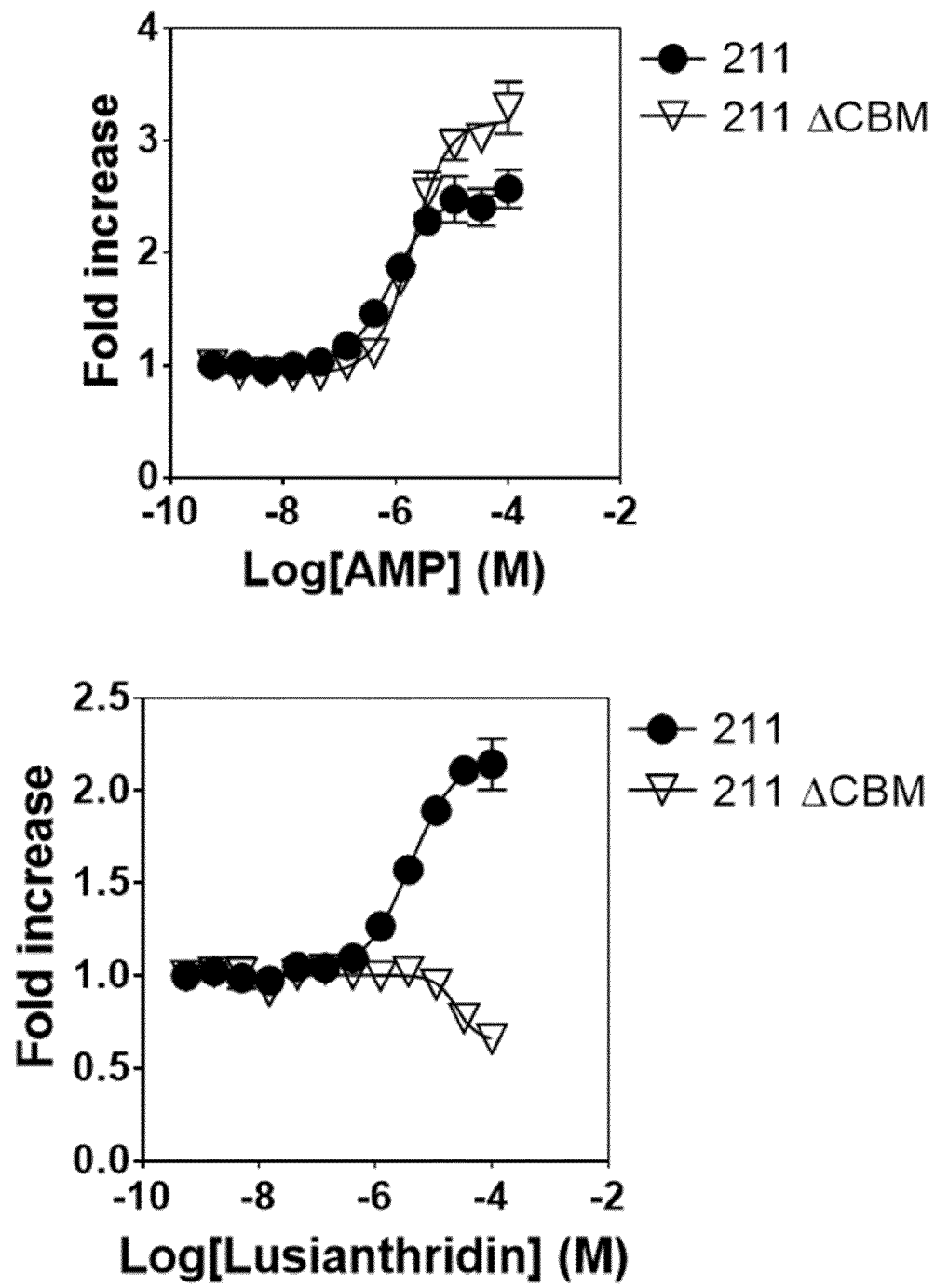
FIG. 4. AMP and Lusianthridin activation of bacterially-expressed AMPKα2β1γ1 (211) or α2β1γ1 complexes with the carbohydrate-binding module (CBM) deleted from the complex (ΔCBM) (211 ΔCBM). Lusianthridin does not activate the α2β1γ1 ΔCBM mutant. The CBM forms an integral part of the ADaM binding site and mediates binding of activators at this site. These data suggest that Lusianthridin activates AMPK at this site.
Figure 5:
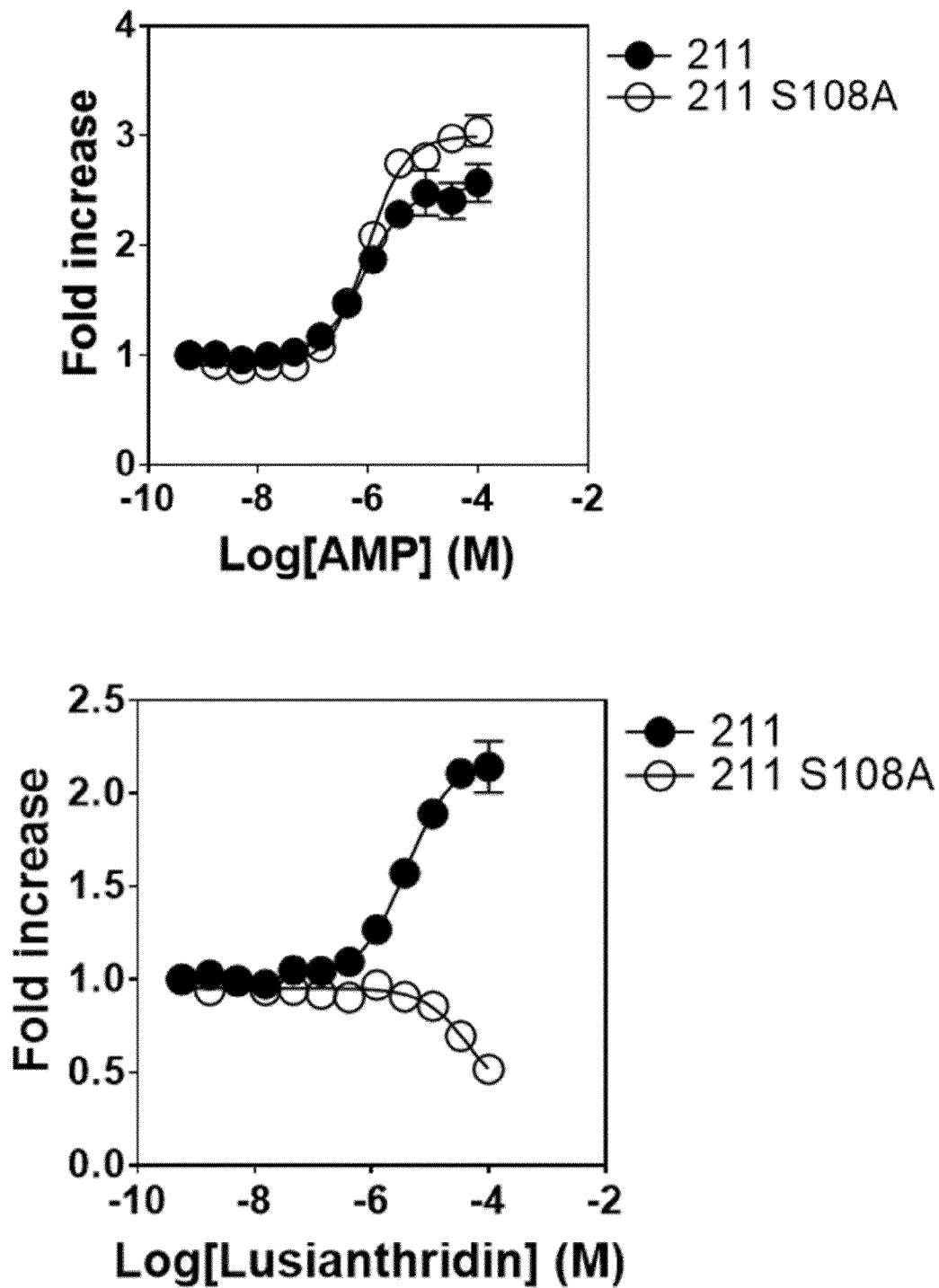
FIG. 5. AMP and Lusianthridin activation of bacterially-expressed AMPKα2β1γ1 (211) or α2β1γ1 complexes harbouring the β1 S108A (211 S108A) mutation. Lusianthridin does not activate AMPK complexes with the S108A mutation. Previously, it has been shown that the S108A mutation interferes with regulation of AMPK at the ADaM binding site. Importantly, the phosphorylated S108 residue forms important interactions between the CBM of the β1 subunit and the kinase domain of the α subunit.
Figure 6:
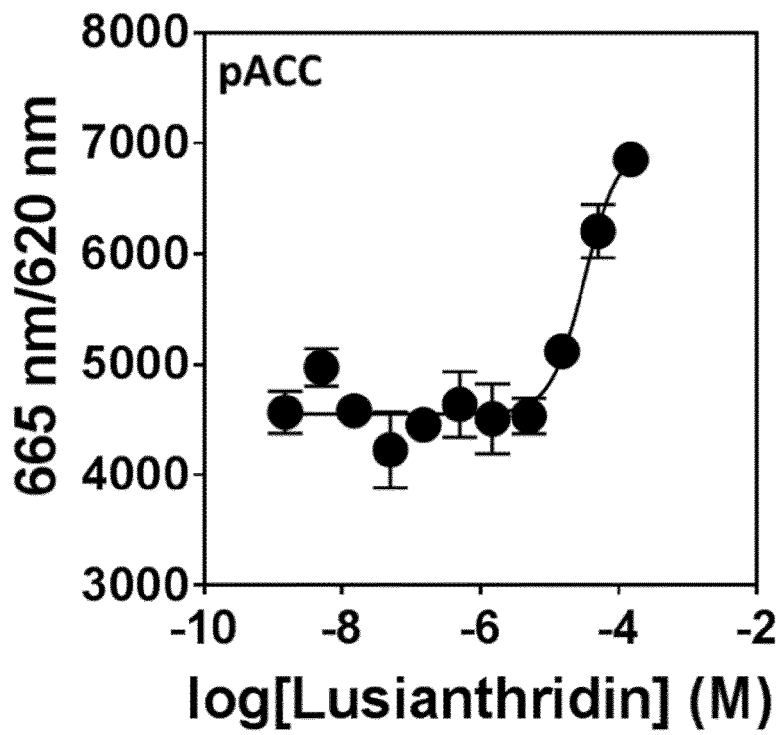
FIG. 6. Lusianthridin increases the phosphorylation of the AMPK substrate, acetyl-CoA carboxylase (ACC), in U2OS Flp-In T-REx mammalian cells.
(a) HTRF assay
(b) Western blot analysis FIG. 7. Lusianthridin increases the phosphorylation of the AMPK substrate, ACC, in mouse primary hepatocytes.
Figure 6:
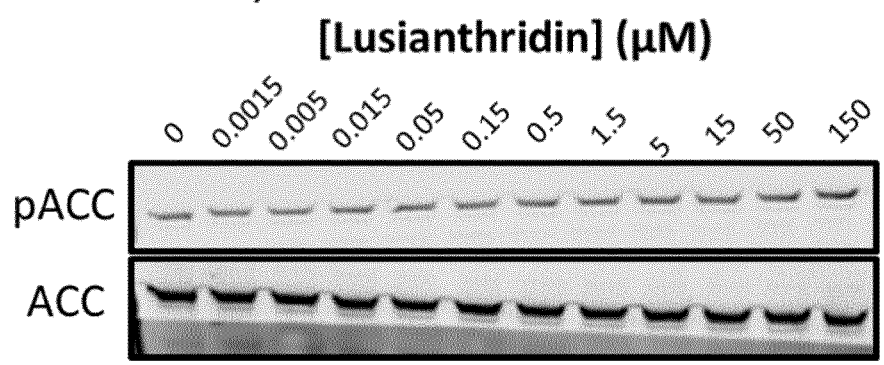

FIG. 6(a) shows that using a pACC HTRF assay kit (Cisbio), Lusianthridin increases the phosphorylation of the AMPK substrate, ACC, in a dose-dependent manner in U2OS Flp-In T-REx mammalian cells. Phosphorylation of ACC is widely used as a cellular indicator of AMPK activity.

FIG. 6(b) shows a Western blot analysis of U2OS Flp-In T-REx lysates that were treated with varying concentrations of Lusianthridin. Lysates were probed using phosphos-specific ACC and total ACC antibodies (Cell signalling). These data indicate that Lusianthridin activates AMPK in cells and this leads to phosphorylation of one its downstream substrates.

Example 4

Lusianthridin Increases the Phosphorylation of the AMPK Substrate, ACC, in Mouse Primary Hepatocytes.

Hepatocyte isolation: The liver was first perfused with 50 ml perfusion buffer (Krebs-Hepes buffer with 0.5 μM EDTA), followed with 50 ml collagenase A buffer (Krebs-Hepes buffer with 5 mM CaCl$_2$ and 0.5 mg/ml collagenase). After passage through a 100 μm mesh, the cell solution was washed several times with cold media and finally the cell culture pellet was resuspended in culture medium (medium 199 (M199)+GlutaMAX, 100 U/ml penicillin G, and 100 μg/ml streptomycin, 0.1% (wt/vol) BSA, 10% FCS, 10 nM insulin, 200 nM triiodothyronine and 500 nM dexamethasone). Hepatocytes were left to attach (3-4 h) and cultured overnight in M199 supplemented with antibiotics and 100 nM dexamethasone. Cells were used for experiments the following morning.

Primary hepatocytes were seeded at 15 K cells in a 96-well plate overnight. Cells were treated for 1 h with varying concentrations of Lusianthridin in media and then cells were lysed in 50 μl of Cisbio lysis buffer #1 supplemented with blocking solution as per the manufacturer's protocol (Cisbio). Cells were lysed for 30 mins at room temperature before 16 μl of lysate was incubated with 4 μl of the HTRF antibodies. Lysates were incubated overnight with the antibody before 665 nm/620 nm ratio was determined using a MolecularDevices i3 plate reader (with a HTRF cartridge add-on).

Figure 7:
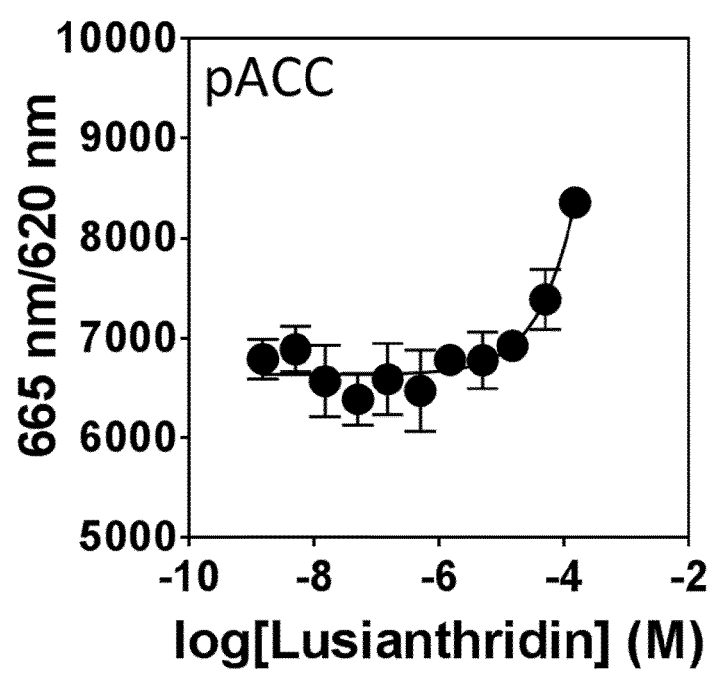

FIG. 7 shows that using a pACC HTRF assay kit (Cisbio), Lusianthridin increases the phosphorylation of the AMPK substrate, ACC, in a dose-dependent manner in primary hepatocytes (1 h incubation at 37 C).

Example 5

Lusianthridin Displays a Dose-Dependent Inhibition of Lipogenesis in Primary Hepatocytes.

For primary hepatocyte isolation see Example 4. For lipogenesis measurements in primary hepatocytes, cells were seeded at 600 K cells per well in a 6-well plate overnight. Media was replaced with fresh M199 media alone for 2 hours prior to incubation with varying concentrations of Lusianthridin for 1 h at 37 C, in the presence of [1-$^{14}$C]-acetate. The incorporation of [$^{14}$C] into fatty acids was determined in the lower organic layer after separation from the aqueous phase. The results are displayed as the disintegrations per min (DPM) per µg of protein.

Figure 8:
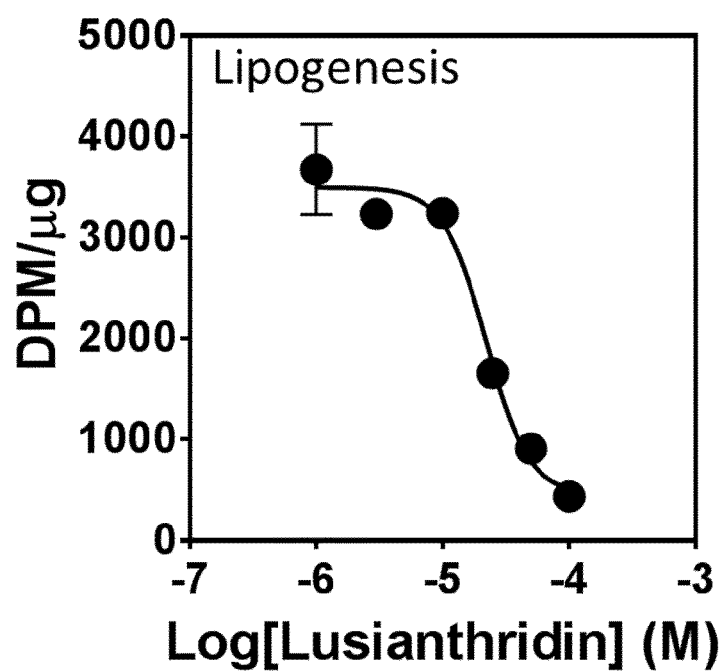
FIG. 8. Lusianthridin displays a dose-dependent inhibition of lipogenesis in primary hepatocytes.

Lipogenesis is controlled by the AMPK substrate ACC, and phosphorylation and inhibition of ACC by AMPK, leads to a decrease in lipogenesis. Lipogenesis was measured in primary hepatocytes by determining the incorporation of $^{14}$C-labelled acetate into fatty acids. Lipogenesis was monitored in the presence or absence of varying concentrations of Lusianthridin for 1 h at 37 C. The results shown in FIG. 8, displayed as the DPM per µg of total protein, that Lusianthridin is able to inhibit lipogenesis in a dose-dependent manner. This observation is consistent with its ability to activate AMPK in hepatocytes, which leads to the phosphorylation and inhibition of ACC. These data are consistent with the ability to Lusianthridin to activate AMPK in both a cell line and primary hepatocytes as previously determined by a HTRF assay and western blot analysis (see examples above).

Example 6

Lusianthridin Increases Glucose Uptake into Differentiated C2C12 Cells.

C2C12 cells were maintained in DMEM GlutaMAX supplemented with 10% (vol/vol) FBS and 100 U/ml penicillin G, and 100 µg/ml streptomycin. C2C12 myoblasts were differentiated into myotubes by 7 days of culture in DMEM GlutaMAX supplemented with 2% (vol/vol) horse serum and antibiotics. Cells were transferred to serum-free media for 24 hours, before equilibrating with bicarbonate-free medium prior to treatment. Cells were treated with Control (DMSO 1% final concentration) or 100 µM Lusianthridin in the presence of $^3$H-2-deoxyglucose (in Krebs-Hepes buffer containing sodium pyruvate). Cells were lysed and the quantity of $^3$H determined in these samples using a scintillation counter.

Figure 9:
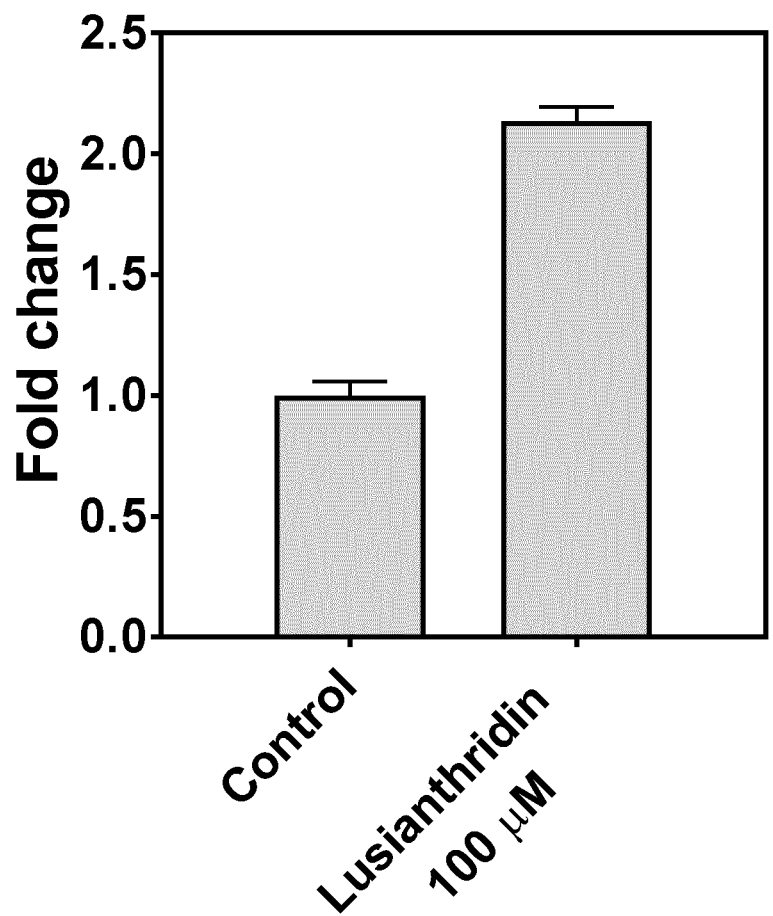
FIG. 9. Lusianthridin increases glucose uptake into differentiated C2C12 cells.

Activation of AMPK in muscle cells has been previously shown to increase glucose uptake. Therefore, it was tested whether activation of AMPK in a differentiated muscle cell line, C2C12 cells, would lead to an increase in glucose uptake. Differentiated C2C12 cells were treated with either control or 100 µM Lusianthridin for 4 h at 37 C. Glucose uptake was determined by monitoring the uptake of $^3$H-2-deoxyglucose into cells. The results in FIG. 9 are displayed as fold increase relative to the control wells. These results show that Lusianthridin causes around a 2-fold increase in glucose uptake into C2C12 cells. These data suggest that the ability of Lusianthridin to activate AMPK in muscle leads to phosphorylation of downstream substrate(s), culminating in the increase in glucose uptake into this muscle cell line. This is consistent with the important role of AMPK in mediating glucose uptake in muscle.

Example 7

Further Dihydrophenanthrene Analogues Directly Allosterically Activate AMPK and Increase Substrate Phosphorylation in Cells.

Figure 10:
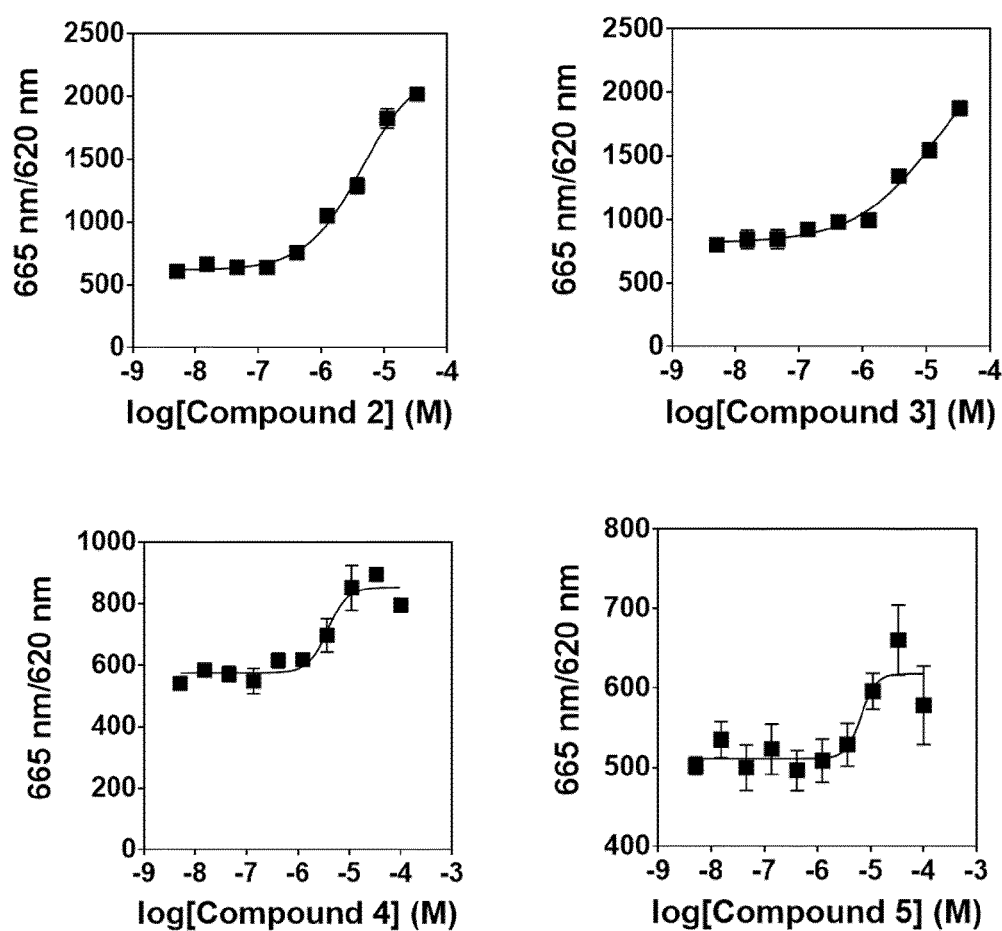
FIG. 10. Compound 2, Compound 3, Compound 4 and Compound 5 activation of bacterially-expressed AMPKα2β1γ1 complexes.

For the AMPK in vitro activity assay, see Example 2. FIG. 10 shows that Compound 2, Compound 3, Compound 4 and Compound 5 activate bacterially-expressed AMPKα2β1γ1 complexes. Similar to Lusianthridin, Compound 4 did not activate β2-containing complexes, the α2β1γ1 ΔCBM mutant and AMPK complexes with the S108A mutation (FIG. 11). Taken together, this suggests that Lusianthridin and Compound 4 share a common activation mechanism and this activity profile is characteristic of ligands that regulate AMPK by binding to the ADaM pocket.

For treatment of U2OS Flp-In T-REx cells see Example 3. FIG. 12 shows that using a pACC HTRF assay kit (Cisbio), Compound 2, Compound 3, Compound 4 and Compound 5 increase the phosphorylation of the AMPK substrate, ACC, in a dose-dependent manner in U2OS Flp-In T-REx mammalian cells.

Example 8

Compound 4 Activates AMPK in Mouse Primary Hepatocytes and Decreases Hepatic Lipogenesis, as Well as Increasing Glucose Uptake into C2C12 Cells.

Mouse primary hepatocytes were isolated (see Example 4) and treated (see Example 5) with varying concentrations of Compound 4 for 1 h at 37 C before the rate of lipogenesis was determined (see Example 5). As shown in FIG. 13, Compound 4 caused a dose-dependent decrease in the rate of lipogenesis, comparable to the effect seen with Lusianthridin.

C2C12 cells were cultured and differentiated into myotubes (see Example 6), before treatment with Compound 4. FIG. 14 shows that Compound 4 caused around a 2-fold increase in glucose uptake, comparable with the effect seen with Lusianthridin.

Example 9

Ability of Lusianthridin to Increase Glucose Uptake in C2C12 Myotubes is Dependent on AMPK In order to test whether the ability of Lusianthridin to increase glucose uptake in C2C12 myotubes is dependent on AMPK, we generated C2C12 cells lacking both isoforms of the catalytic AMPKα subunit, AMPKα1α2-/-. C2C12 AMPK α1α2 double knockout cell lines were generated by transient transfection of wild type cells with plasmids containing Cas9 enzyme linked to green fluorescent protein expression and Cas9 guide RNA sequences targeting the murine AMPK α1 subunit (sc-430618, SantaCruz) and the murine AMPK α2 subunit (sc-430803, SantaCruz). Cells positive for green fluorescent protein expression were single cell sorted by flow cytometry into 96-well plates containing growth medium and analysed for loss of AMPK signaling following expansion of the clones.

Differentiated C2C12 AMPKα1α2+/+ and AMPKα1α2-/- cells were treated with either vehicle (0.2% DMSO), 30 µM or 100 µM Lusianthridin for 1 h at 37° C. In addition, the insulin-dependent/AMPK-independent glucose uptake was also assessed by treating C2C12 cells with 300 nM Insulin for 1 h in the presence or absence of the 15 nM Wortmanin, an inhibitor of insulin-signalling. Finally, differentiated C2C12 AMPKα1α2+/+ and AMPKα1α2-/- cells were treated with either vehicle (0.2% DMSO) or 100 µM Lusianthridin in the presence or absence of 15 nM Wortmanin for 1 h at 37° C. For the Wortmanin experiments, differentiated C2C12 cells were pre-incubated with DMSO or Wortmanin for 1 h prior to treatment.

Glucose uptake was determined by monitoring the uptake of 3H-2-deoxyglucose into cells. C2C12 AMPKα1α2+/+ and AMPKα1α2-/- cells were maintained in DMEM GlutaMAX supplemented with 20% (vol/vol) FBS and 100 U/ml penicillin G, and 100 µg/ml streptomycin. C2C12 myoblasts were differentiated into myotubes by 5-7 days of culture in DMEM GlutaMAX supplemented with 1% (vol/vol) horse serum and antibiotics. Cells were transferred to serum-free media for 24 hours, before equilibrating with bicarbonate-free medium prior to treatment. Cells were treated in the presence of $^3$H-2-deoxyglucose (in Krebs-Hepes buffer containing sodium pyruvate). Cells were lysed and the quantity of $^3$H determined in these samples using a scintillation counter. Fold change in glucose uptake was determined by dividing the counts per minute obtained for each treatment condition by the counts per minute obtained in the vehicle control condition.

The results in the FIGS. 15 to 17 are displayed as fold change relative to the control wells. The results in FIGS. 15 and 16 show that treatment of C2C12 AMPKα1α2+/+ cells with Lusianthridin and insulin lead to an increase in glucose uptake. Insulin-stimulated glucose uptake was unaffected in the AMPKα1α2-/- cells, but as expected its effects are abolished by treatment with Wortmanin (FIG. 16).

In contrast, Wortmanin had no effect on the ability of Lusianthridin to increase glucose uptake in AMPKα1α2+/+ cells, suggesting that this compound does not increase glucose uptake through the insulin-signalling pathway (FIG. 17). In contrast, Lusianthridin-stimulated glucose uptake was abolished in AMPKα1α2-/- cells (FIG. 15). Taken together, these data suggest that the ability of Lusianthridin to increase glucose uptake into C2C12 cells is dependent on its ability to activate AMPK.

Example 10

Lusianthridin Does Not Cause Cytotoxicity in Mouse Primary Hepatocytes.

For cytotoxicity experiments in primary hepatocytes, cells were seeded at 20 K cells per well in a 96-well plate overnight in M199 media. Hepatocytes were incubated with varying concentrations of Lusianthridin, Oligomycin or FCCP for 1 h at 37 C. The media was changed for media without phenol red, before performing an MTT assay as per the manufacturer's instructions (Thermo fisher, V131154). The MTT assay is a calorimetric assay that is routinely used to measure the cytotoxicity of compounds in cells. The results shown in the FIG. 18 show that at all the concentrations of Lusianthridin tested, there was no change in cell viability. In contrast, two known toxic compounds, Oligomycin and FCCP (carbonyl cyanide P-(trifluoromethoxy) phenylhydrazone), caused a robust decrease in cell viability. Taken together, this suggests that Lusianthridin does not have a cytotoxic effect on mouse primary hepatocytes up to a final concentration of 100 μM.

Example 11

Lusianthridin Does Not Activate a Complex Containing a Mutation at the Allosteric Drug and Metabolite (ADaM) Site in Cells (S108A).

AMPKβ1/β2 double knockout U2-OS Flp-In™ T-Rex™ cell lines were generated by Horizon Discovery (Cambridge, UK). Cells were genotyped and analysed by western blotting to confirm that there was a complete knockout of AMPKβ1/β2. We took these AMPKβ1/β2 double knockout cells, and re-introduced the expression of human β1 wild-type (WT) or a β1 Serine 108 to alanine mutation (S108A). This was achieved using the Flp-In™ system (Invitrogen) present in this cell line and stable cells expressing β1 WT or a β1 S108A mutant were generated according to the manufacturers' protocols. Re-expression of the β1 subunit was confirmed by western blot analysis.

Cells stably expressing β1 WT or a β1 S108A mutant were treated with varying concentrations of Lusianthridin and subjected to the pACC HTRF (Cisbio) assay or western blot analysis to determine phosphorylation of the AMPK substrate, ACC, in cells lysates. Western blots were quantified using the LI-COR odyssey system and shown as the ratio of the antibody signal from pACC divided by total ACC.

As shown in FIGS. 19 and 20, Lusianthridin was able to dose-dependently increase pACC in cells stably expressing the β1 WT. In contrast, Lusianthridin was not able to increase pACC in cells expressing the β1 S108A mutant. This cellular data is consistent with our in vitro data showing that Lusianthridin cannot allosterically activate recombinant α2β1γ1 S108A complexes. Taken together, we show that in vitro and in cells, Lusianthridin activates AMPK by binding to the ADaM pocket of AMPK separate from the nucleotide-binding site in the AMPKγ subunit.

The invention claimed is:

1. A method for activation of AMPK to treat, and/or reduce a severity of non-alcoholic fatty liver disease (NAFLD) in a subject in need thereof, the method comprising administering to the subject a compound having the general formula I,

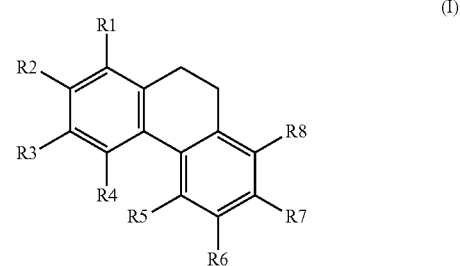

wherein R1, R2, R3, R4, R5, R6, R7, and R8 are each independently selected from the group consisting of H; OH; OMe; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; a carboxylic acid; an ester; a primary, secondary, or tertiary amine; a primary or secondary amide; a cyano; a nitro; a sulfonate; a sulfate; an optionally substituted and/or optionally branched $C_1$ to $C_{20}$ alkyl; an optionally substituted and/or optionally branched, $C_2$ to $C_{20}$ alkenyl; an optionally substituted and/or optionally branched, $C_4$ to $C_{20}$ polyalkenyl; an optionally substituted and/or optionally branched $C_2$ to $C_{20}$ alkynyl, or an optionally substituted and/or optionally branched $C_4$ to $C_{20}$ polyalkynyl, and/or optionally a $OCH_3$ group can cyclize with a neighboring OH group to form a methylene dioxy bridge.

2. The method according to claim 1, wherein R1, R2, R3, R6, R7, and R8 are each independently selected from the group consisting of H; OH; OMe; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; a carboxylic acid; an ester; a primary, secondary, or tertiary amine; a primary or secondary amide; a cyano; a nitro; a sulfonate; a sulfate; an optionally substituted and/or optionally branched $C_1$ to $C_{20}$ alkyl; an optionally substituted and/or optionally branched, $C_2$ to $C_{20}$ alkenyl; an optionally substituted and/or optionally branched, $C_4$ to $C_{20}$ polyalkenyl; an optionally substituted and/or optionally branched $C_2$ to $C_{20}$ alkynyl, or an optionally substituted and/or optionally branched $C_4$ to $C_{20}$ polyalkynyl; R4 and R5 are each independently H; OH; O-glycoside; C-glycoside; acylated O-glycoside; acylated C-glycoside; sulfated O-glycoside; sulfated C-glycoside; a halogen; a primary, secondary, or tertiary alcohol; a ketone; an aldehyde; a carboxylic acid; an ester; a primary, secondary, or tertiary amine; a primary or secondary amide; a cyano; a nitro; a sulfonate; a sulfate; an optionally substituted and/or optionally branched $C_1$ to $C_{20}$alkyl; an optionally substituted and/or optionally branched, $C_2$ to $C_{20}$ alkenyl; an optionally substituted and/or optionally branched, $C_4$ to $C_{20}$ polyalkenyl; an optionally substituted and/or optionally branched $C_2$ to $C_{20}$ alkynyl, or an optionally substituted and/or optionally branched $C_4$ to $C_{20}$ polyalkynyl, and/or optionally a $OCH_3$ group can cyclize with a neighboring OH group to form a methylene dioxy bridge.

3. The method according to claim 1, wherein R1, R2, R3, R4, R5, R6, R7, and R8 are each independently selected from the group consisting of H; OH; OMe; O-glycoside; a halogen; an aldehyde; a carboxylic acid; a primary, secondary, or tertiary amine; a primary or secondary amide; a cyano; a nitro; a sulfonate; a sulfate; an optionally substituted and/or optionally branched $C_1$ to $C_{20}$ alkyl; an optionally substituted and/or optionally branched, $C_2$ to $C_{20}$ alkenyl; an optionally substituted and/or optionally branched, $C_4$ to $C_{20}$ polyalkenyl; an optionally substituted and/or optionally branched $C_2$ to $C_{20}$ alkynyl, or an optionally substituted and/or optionally branched $C_4$ to $C_2$ polyalkynyl, and/or optionally a $OCH_3$ group can cyclize with a neighboring OH group to form a methylene dioxy bridge.

4. The method according to claim 1, wherein R1, R2, R3, R4, R5, R6, R7, and R8 are each independently selected from the group consisting of H; Me; OH; OMe; $OCH_2CH=CH_2$; O-glycoside; a sulfate; a halogen; CHO; $CH_2OH$; COOH, $CONH_2$, $COCH_3$; $CH=CH_2$; $CH_2—CH=C(CH_3)_2$; $CH(CH_3)_2$; $CH=CH—CHO$; $CH(CH_3)—OH$; $CH(CH_3)—OMe$; $CH(CH_3)—OC_2H_5$; $CH(CH_3)—O—CH_2—CH=C(CH_3)—(CH_2)_3—CH(CH_3)—(CH_2)_3—CH(CH_3)—(CH_2)_3—CH(CH_3)_2$; 4-hydroxybenzyl; 4-hydroxy-3-methoxybenzyl; 4-hydroxybenzoyl; 4-hydroxybenzoyl glycoside, and/or optionally a $OCH_3$ group can cyclize with a neighboring OH group to form a methylene dioxy bridge.

5. The method having the general formula I according to claim wherein R1, R2, R3, R6, R7, and R8 are each independently selected from the group consisting of H; OH; OMe; O-glycoside; a halogen; an aldehyde; a carboxylic acid; a primary, secondary, or tertiary amine; a primary or secondary amide; a cyano; a nitro; a sulfonate; a sulfate; an optionally substituted and/or optionally branched $C_1$ to $C_{20}$ alkyl; an optionally substituted and/or optionally branched, $C_2$ to $C_{20}$ alkenyl; an optionally substituted and/or optionally branched, $C_4$ to $C_{20}$ polyalkenyl; an optionally substituted and/or optionally branched $C_2$ to $C_2$ alkynyl, or an optionally substituted and/or optionally branched $C_4$ to $C_{20}$ polyalkynyl; R4 and R5 are each independently H; OH; O-glycoside; a halogen; an aldehyde; a carboxylic acid; a primary, secondary, or tertiary amine; a primary or secondary amide; a cyano; a nitro; a sulfonate; a sulfate; an optionally substituted and/or optionally branched $C_1$ to $C_{20}$ alkyl; an optionally substituted and/or optionally branched, $C_2$ to $C_{20}$ alkenyl; an optionally substituted and/or optionally branched, $C_4$ to $C_{20}$ polyalkenyl; an optionally substituted and/or optionally branched $C_2$ to $C_{20}$ alkynyl, or an optionally substituted and/or optionally branched $C_4$ to $C_{20}$ polyalkynyl, and/or optionally a $OCH_3$ group can cyclize with a neighboring OH group to form a methylene dioxy bridge.

6. The method according to claim 1, wherein R1, R2, R3, R6, R7, and R8 are each independently selected from the group consisting of H; Me; OH; OMe; $OCH_2CH=CH_2$; O-glycoside; a sulfate; a halogen; CHO; $CH_2OH$; COOH, $CONH_2$, $COCH_3$; $CH=CH_2$; $CH_2—CH=C(CH_3)_2$; $CH(CH_3)_2$; $CH=CH—CHO$; $CH(CH_3)—OH$; $CH(CH_3)—OMe$; $CH(CH_3)—OC_2H_5$; $CH(CH_3)—O—CH_2—CH=C(CH_3)—(CH_2)_3—CH(CH_3)—(CH_2)_3—CH(CH_3)—(CH_2)_3—CH(CH_3)_2$; 4-hydroxybenzyl; 4-hydroxy-3-methoxybenzyl; 4-hydroxybenzoyl; 4-(addedhydroxybenzoyl glycoside; R4 and R5 are each independently H; Me; OH; $OCH_2CH=CH_2$; O-glycoside; a sulfate; a halogen; CHO; $CH_2OH$; COOH, $CONH_2$, $COCH_3$; $CH=CH_2$; $CH_2—CH=C(CH_3)_2$; $CH(CH_3)_2$; $CH=CH—CHO$; $CH(CH_3)—OH$; $CH(CH_3)—OMe$; $CH(CH_3)—OC_2H_5$; $CH(CH_3)—O—CH_2—CH=C(CH_3)—(CH_2)_3—CH(CH_3)—(CH_2)_3—CH(CH_3)—(CH_2)_3—CH(CH_3)_2$; 4-hydroxybenzyl; 4-hydroxy-3-methoxybenzyl; 4-hydroxybenzoyl; 4-hydroxybenzoyl glycoside, and/or optionally a $OCH_3$ group can cyclize with a neighboring OH group to form a methylene dioxy bridge.

7. The method according to claim 1, wherein R1, R2, R3, R6, R7, and R8 are each independently selected from the group consisting of H; Me; OH; OMe; $OCH_2CH=CH_2$; O-glycoside; a sulfate; Br; CHO; $CH_2OH$; COOH, $CONH_2$, $COCH_3$; $CH=CH_2$; $CH_2—CH=C(CH_3)_2$; $CH(CH_3)_2$; $CH=CH—CHO$; $CH(CH_3)—OH$; $CH(CH_3)—OCH_3$; $CH(CH_3)—OC_2H_5$; $CH(CH_3)—O—CH_2—CH=C(CH_3)—(CH_2)_3—CH(CH_3)—(CH_2)_3—CH(CH_3)—(CH_2)_3—CH(CH_3)_2$; 4-hydroxybenzyl; 4-hydroxy-3-methoxybenzyl; 4-hydroxybenzoyl; 4-hydroxybenzoyl glycoside; R4 and R5 are each independently H; Me; OH; $OCH_2CH=CH_2$; O-glycoside; a sulfate; Br; CHO; $CH_2OH$; COOH, $CONH_2$, $COCH_3$; $CH=CH_2$; $CH_2—CH=C(CH_3)_2$; $CH(CH_3)_2$; $CH=CH—CHO$; $CH(CH_3)—OH$; $CH(CH_3)—OCH_3$; $CH(CH_3)—OC_2H_5$; $CH(CH_3)—O—CH_2—CH=C(CH_3)—(CH_2)_3—CH(CH_3)—(CH_2)_3—CH(CH_3)—(CH_2)_3—CH(CH_3)_2$; 4-hydroxybenzyl; 4-hydroxy-3-methoxybenzyl; 4-hydroxybenzoyl; 4-hydroxybenzoyl glycoside, and/or optionally a $OCH_3$ group can cyclize with a neighboring OH group to form a methylene dioxy bridge.

8. The method according to claim 1, wherein said compound is selected from the group consisting of:
  (i) Lusianthridin known as 7-Methoxy-9,10-dihydrophenanthrene-2,5-diol;
  (ii) 7-Methoxy-9,10-dihydrophenanthrene-2,3,5-triol;
  (iii) 2,5-Phenanthrenediol, 9,10-dihydro, 9,10-Dihydrophenanthrene-2,5-diol;
  (iv) 9,10-Dihydrophenanthrene-2,4,7-triol, 9,10-Dihydro-2,4,7-phenanthrenetriol, 2,4,7-Trihydroxy-9,10-dihydrophenanthrene, 2,4,7-Phenanthrenetriol, 9,10-dihydro; and
  (v) Cannithrene 1, Cannabidihydrophenanthrene, 9,10-Dihydro-7-methoxy-3,5-phenanthrenediol, 3,5-Phenanthrenediol, 9,10-dihydro-7-methoxy, 7-Methoxy-9,10-dihydrophenanthrene-3,5-diol.

9. The method according to claim 1, wherein the subject is a human or a companion animal.

10. The method according to claim 9, wherein the subject is a human.

11. The method according to claim 9, wherein the activation of the AMPK further improves a condition, disorder, or disease selected from the group consisting of cardiometabolic health, obesity, type 2 diabetes, cardiovascular disease, and cancer.

12. The method according to claim 1, wherein the activation of the AMPK is a direct activation mechanism.

13. The method according to claim 1, wherein the activation of the AMPK occurs in muscle and/or liver tissues.

14. The method according to claim 1, wherein the AMPK comprises an α2 subunit, a β1 subunit, and a γ1 subunit.

15. The method according to claim 1, wherein the compound is obtained from a plant or plant extract.

16. A method according to claim 1, wherein the compound of formula I is administered as a medicament.

17. The method according to claim 1, wherein the compound is administered in a composition selected from the group consisting of a food, a beverage, and a dietary supplement.

18. A method according to claim 16, wherein the compound of general formula I is selected from the group consisting of:
  (i) Lusianthridin known as 7-Methoxy-9, 10-dihydrophenanthrene-2,5-diol;
  (ii) 7-Methoxy-9,10-dihydrophenanthrene-2,3,5-triol;
  (iii) 2,5-Phenanthrenediol, 9,10-dihydro, 9,10-Dihydrophenanthrene-2,5-diol;
  (iv) 9,10-Dihydrophenanthrene-2,4,7-triol, 9,10-Dihydro-2,4,7-phenanthrenetriol, 2,4,7-Trihydroxy-9,10-dihydrophenanthrene, 2,4,7-Phenanthrenetriol, 9,10-dihydro;
  (v) Cannithrene 1, Cannabidihydrophenanthrene, 9,10-Dihydro-7-methoxy-3,5-phenanthrenediol, 3,5-Phenanthrenediol, 9,10-dihydro-7-methoxy, 7-Methoxy-9,10-dihydrophenanthrene-3,5-diol.

* * * * *